United States Patent [19]
Breakefield et al.

[11] Patent Number: 5,407,821
[45] Date of Patent: Apr. 18, 1995

[54] GENETIC DIAGNOSIS OF TORSION DYSTONIA

[75] Inventors: Xandra O. Breakefield, Newton; Laurie Ozelius, Cambridge, both of Mass.

[73] Assignee: The General Hospital Corporation, Boston, Mass.

[21] Appl. No.: 725,083

[22] Filed: Jul. 3, 1991

Related U.S. Application Data

[63] Continuation-in-part of Ser. No. 353,432, May 18, 1989, abandoned.

[51] Int. Cl.$^6$ .......................... C12Q 1/68; C12P 19/34
[52] U.S. Cl. .......................... 435/6; 435/91.2; 935/77; 935/78; 436/63; 436/811; 436/501
[58] Field of Search ............... 435/5, 91.2; 436/63, 436/501; 536/27, 28, 29, 24.31; 935/6, 7, 8, 76, 77, 78

[56] References Cited
U.S. PATENT DOCUMENTS

4,666,828  5/1987  Gusella .................................. 435/6

OTHER PUBLICATIONS

Breakfield et al. J of Neurogenetics 3 (1986) 159–175.
Kramer et al. Adv. in Neurology, 50: Dystonia 2, pp. 57–60 (1988).
Ozelins et al. Neuron, 2(5) 1427–34 (1989).
Adams, L. M. et al., "Possible Involvement of Brain Noradrenergic Neurons in Dystonia", *Advances In Neurology* 50:313-333 (1988).
Beaudet, A. L. et al., "Dispersion of Argininosuccinate-Synthetase-Like Human Genes to Multiple Autosomes and the X Chromosome", *Cell* 30:287-293 (Aug. 1982).
Bech-Hansen, N. T. et al., "TaqI RFLP In Human Adneylate Kinase-1 (AK1) Gene Region On Chromosome 9", *Nucleic Acids Research* 17(10):4004 (1989).
Breakefield, X. O. et al., "Linkage Analysis in a Family with Dominantly Inherited Torsion Dystonia: Exclusion of the Pro-Opiomelanocortin and Glutamic Acid Decarboxylase Genes and Other Chromosomal Regions Using DNA Polymorphisms", *J. of Neurogenetics* 3:159-175 (1986).
Breakefield, X. O. et al., "Human Dystonia Gene Found On Chromosome 9q32-34", *Soc. Neurosci. Abstr.* 15(1):653 (1989).
Bressman, Susan B. et al., "Inheritance of Idiopathic Torsion Dystonia Among Ashkenazi Jews", *Advances in Neurology* 50:45-56 (1988).
Bressman, Susan B. et al., "Paroxysmal Non-Kinesigenic Dystonia", *Advances in Neurology* 50:403-413 (1988).
Brin, Mitchell F. et al., "Autosomal Dominant Dystonia in a Large North American Family: Clinical Features", *Neurology* 37(Suppl 1):137 (Mar. 1987).
Burke, Robert E. et al., "Analysis of the Clinical Course of Non-Jewish, Autosomal Dominant Torsion Dystonia", *Movement Disorders* 1(3):163-178 (1986).
Calne, D. B. et al., "Secondary Dystonia", *Advances in Neurology* 50:9-33 (1988).
Carlson, M. et al., "Isolation and Mapping of a Polymorphic DNA Sequence pMCT136 On Chromosome 9q(D9S10)", *Nucleic Acids Research* 15(24):20613 (1987).
Chakravarti, Aravinda et al., "Nonuniform Recombination within the Human β-Globin Gene Cluster", *Am. J. Hum. Genet.* 36:1239-1258 (1984).
Donis-Keller, H. et al., "A Genetic Linkage Map of the Human Genome", *Cell* 51:319-337 (Oct. 23, 1987).
Duchen, L. W., "*Dystonia musculorum*—An Inherited Disease of the Nervous System in the Mouse", *Adv. Neurol.* 14:353-365 (1976).

(List continued on next page.)

*Primary Examiner*—Margaret Parr
*Assistant Examiner*—Carla Myers
*Attorney, Agent, or Firm*—Sterne, Kessler, Goldstein & Fox

[57] ABSTRACT

Methods are provided for detecting the presence of a gene for torsion dystonia in a human subject. Furthermore, a haplotype which is associated with torsion dystonia is disclosed. Methods and kits for the detection of torsion dystonia in a subject are additionally provided.

23 Claims, 11 Drawing Sheets

OTHER PUBLICATIONS

Eldridge, Roswell, "The Torsion Dystonias: Literature Review and Genetic and Clinical Studies", *Neurology* 20:1–78 (Nov. 1970).

Falk, C. T. et al., "Linkage Studies in Families with Dystonia: Linkage Analysis as a Tool to Locate and Characterize the Gene(s) for Dystonia", *Advances in Neurology* 50:83–92 (1988).

Forsgren, Lars et al., "Autosomal Dominant Torsion Dystonia in a Swedish Family", *Advances in Neurology* 50:83–92 (1988).

Fujita, Ricardo et al., "Additional Polymorphisms At Marker Loci D9S5 and D9S15 Generate Extended Haplotypes In Linkage Disequilibrium with Friedreich Ataxia", *PNAS USA* 87:1796–1800 (Mar. 1990).

Hoffman, Eric P. et al., "Dystrophin: The Protein Product of the Duchenne Muscular Dystrophy Locus", *Cell* 51:919–928 (Dec. 24, 1987).

Jankovic, J. et al., "Brain Neurotransmitters in Dystonia", *New England Journal of Mecicine* 316:278–279 (1987).

Jeffreys, Alec J. et al., "Hypervariable 'Minisatellite' Regions In Human DNA", *Nature* 314:67–73 (Mar. 7, 1985).

Johnson, Warren et al., "Studies On *Dystonia musculorum* Deformans", *Archives of Neurology* 7:301–313 (Oct. 1962).

Kerem, Bat-Sheva et al., "Identification of the Cystic Fibrosis Gene: Genetic Analysis", *Science* 245:1073–1080 (Sep. 8, 1989).

Kramer, P. L. et al., "Exclusion of Autosomal Dominant Dystonia Gene From Large Regions of Chromosomes 11p, 13q, and 21q by Multi-Point Linkage Analysis", *Genetic Epidemiology* 4:377–386 (1987).

Kramer, P. L. et al., "Molecular Genetics of an Autosomal Dominant Form of Torsion Dystonia", *Advances in Neurology* 50:57–66 (1988).

Kramer, P. L. et al., "Dystonia Gene in Ashkenazi Jewish Population Is Located On Chromosome 9q32–34", *Annals of Neurology* 27(2):114–120 (1990).

Kurlan, Roger et al., "Myoclonus and Dystonia: A Family Study", *Advances in Neurology* 50:385–389 (1988).

Kwiatkowski, D. et al., "Plasma and Cytoplasmic Gelsolins are Encoded by a Single Gene and Contain a Duplicated Actin-Binding Domain", *Nature* 323:455–458 (Oct. 2, 1986).

Kwiatkowski, D. et al., "Localization of Gelsolin Proximal to ABL On Chromosome 9", *Am. J. Hum. Genet.* 42:565–572 (1988).

Kwiatkowski, David J. et al., "Identification of a Highly Polymorphic Microsatellite VNTR Within the Argininosuccinate Synthetase Locus: Exclusion of the Dystonia Gene On 9q32–34 as the Cause of Dopa-Responsive Dystonia", *Am. J. Hum. Genet.* 48:121–128 (1991).

Kwiatkowski, David J. et al., "Dinucleotide Repeat Polymorphism at the GSN Locus (9q32–34)", *Nucleic Acids Research* 19(4):967 (Feb. 25, 1991).

Lander, Eric S. et al., "Mapmaker: An Interactive Computer Package for Consturcting Primary Genetic Linkage Maps of Experimental and Natural Populations", *Genomics* 1:174–181 (1987).

Lathrop, G. M. et al., "Efficient Computations In Multilocus Linkage Analysis", *Am. J. Hum. Genetics* 42:498–505 (1988).

Lathrop, M. et al., "A Mapped Set of Genetic Markers for Human Chromosome 9", *Genomics* 3:361–366 (1988).

Lee, Lillian V. et al., "Torsion Dystonia In Panay, Philippines", *Advances in Neurology* 14:137–151 (1976).

Lee, Wen-Hwa et al., "The Retinoblastoma Susceptibility Gene Encodes a Nuclear Phosphoprotein Associated with DNA Binding Activity", *Nature* 329:642–645 (Oct. 15, 1987).

Litt, Michael et al., "A Hypervariable Microsatellite Revealed By In Vitro Amplification of a Dinucleotide Repeat Within the Cardiac Muscle Actin Gene", *Am. J. Hum. Genet.* 44:397–401 (1989).

Lizardi, P. M. et al., "Exponential Amplification of Recombinant-RNA Hybridization Probes", *Bio/Tech* 6:1197–1202 (Oct. 1988).

Lorden, J. F. et al., "Neuropharmacological Correlates of the Motor Syndrome of the Genetically Dystonic (dt) Rat", *Advances in Neurology* 50:277–297 (1988).

Marsden, C. D. et al., "The Anatomical Basis of Symptomatic Hemidystonia", *Brain* 108:463–483 (1985).

Nakamura, Y. et al., "Variable Number of Tandem Repeat (VNTR) Markers for Human Gene Mapping", *Science* 235:1616–1622 (Mar. 27, 1987).

Northrup, Hope et al., "Multilocus Linkage Analysis with the Human Argininosuccinate Synthetase Gene", *Genomics* 5:442–444 (1989).

Nygaard, Torbjoern G. et al., "Dopa-Responsive Dystonia", *Advances in Neurology* 50:377–384 (1988).

Ozelius, Laurie et al., "Human Gene for Torsion Dystonia Located On Chromosome 9q32–34", *Neuron* 2:1427–1434 (May 1989).

Quinn, N. P. et al., "Hereditary Myoclonic Dystonia, Hereditary Torsion Dystonia and Hereditary Essential Myoclonus: An Area of Confusion", *Advances in Neurology* 50:391–401 (1988).

Risch, Neil J. et al., "Segregation Analysis of Idiopathic Torsion Dystonia in Ashkenazi Jews Suggests Autosomal Dominant Inheritance", *Am. J. Hum. Genet.* 46:533–538 (1990).

Schuback, D. E. et al., "RFLP for Human DBH (Dopamine Beta-Hydroxylase)", *Nucleic Acids Research* 18(2):387 (1990).

Segawa, Masaya et al., "Hereditary Progressive Dystonia with Marked Diurnal Fluctuation", *Advances in Neurology* 14:215–233 (1976).

Weber, James L. et al., "Abundant Class of Human DNA Polymorphisms Which Can Be Typed Using the Polymerase Chain Reaction", *Am. J. Hum. Genet.* 44:388–396 (1989).

Weber, James L. "Informativeness of Human (dC–dA)$_n$ (dG–dT)$_n$ Polymorphisms", *Genomics* 7:524–530 (1990).

White, R. et al., "Construction of Linkage Maps with DNA Markers for Human Chromosomes", *Nature* 313:101–105 (Jan. 10, 1985).

Wilson, A. F. et al., "Linkage of a Gene Regulating Dopamine-$\beta$-Hydroxylase Activity and the ABO Blood Group Locus", *Am. J. Hum. Genet.* 42:160–166 (1988).

Zilber, Nelly et al., "Inheritance of Idiopathic Torsion Dystonia Among Jews", *Journal of Medical Genetics* 21:13–20 (1984).

Zuffardi, Orsetta et al., "Regional Assignment of the Loci for Adenylate Kinase to 9q32 and for $\alpha_1$-Acid Glycoprotein to 9q31–9q32", *Human Genetics* 82:17–19 (1989).

Bishop, J. E., "Scientists Close In on Gene That Causes Dystonia, a Mysterious Nerve Disorder," *The Wall Street Journal*, p. B4 (May 19, 1989).

Bressman, S. B. et al., "Genetic linkage analysis in primary torsion dystonia,", *Neurology* 34:1490–1493 (Nov. 1984).

Craig, S. P. et al., "Localization of the human dopamine beta hydroxylase (DBH) gene to chromosome 9q34," *Cytogenet. Cell. Genet.* 48:48–50 (1988).

Kumlin-Wolf, E. et al., "Isolation and mapping of a polymorphic DNA sequence pEKZ19.3 on chromosome 9q (D9S17)," *Neucleic Acids Researchy* 15(24):10610 (1987).

Kwiatkowski, D. J. et al., "Muscle Is The Major Source of Plasma Gelsolin," *J. Biol. Chem.* 263(17):8239–8243 (Jun. 15, 1988).

Partington, M. W. et al., "X-Linked Mental Retardation With Dystonic Movements Of The Hands," *Am. J. Med. Genet.* 30:251–262 (1988).

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 2608 base pairs
        (B) TYPE: nucleic acid
        (C) STRANDEDNESS: both
        (D) TOPOLOGY: both (ix) FEATURE:
        (A) NAME/KEY: CDS
        (B) LOCATION: 15..2363

(xi) SEQUENCE DESCRIPTION: SEQ ID NO:1:

```
GCCGTGTCGC CACC ATG GCT CCG CAC CGC CCC GCG CCC GCG CTG CTT TGC              50
              Met Ala Pro His Arg Pro Ala Pro Ala Leu Leu Cys
                1           5                   10

GCG CTG TCC CTG GCG CTG TGC GCG CTG TCG CTG CCC GTC CGC GCG GCC              98
Ala Leu Ser Leu Ala Leu Cys Ala Leu Ser Leu Pro Val Arg Ala Ala
         15                  20                  25

ACT GCG TCG CGG GGG GCG TCC CAG GCG GGG GCG CCC CAG GGG CGG GTG            146
Thr Ala Ser Arg Gly Ala Ser Gln Ala Gly Ala Pro Gln Gly Arg Val
         30                  35                  40

CCC GAG GCG CGG CCC AAC AGC ATG GTG GTG GAA CAC CCC GAG TTC CTC            194
Pro Glu Ala Arg Pro Asn Ser Met Val Val Glu His Pro Glu Phe Leu
 45                  50                  55                  60

AAG GCA GGG AAG GAG CCT GGC CTG CAG ATC TGG CGT GTG GAG AAG TTC            242
Lys Ala Gly Lys Glu Pro Gly Leu Gln Ile Trp Arg Val Glu Lys Phe
                 65                  70                  75

GAT CTG GTG CCC GTG CCC ACC AAC CTT TAT GGA GAC TTC TTC ACG GGC            290
Asp Leu Val Pro Val Pro Thr Asn Leu Tyr Gly Asp Phe Phe Thr Gly
             80                  85                  90

GAC GCC TAC GTC ATC CTG AAG ACA GTG CAG CTG AGG AAC GGA AAT CTG            338
Asp Ala Tyr Val Ile Leu Lys Thr Val Gln Leu Arg Asn Gly Asn Leu
         95                 100                 105

CAG TAT GAC CTC CAC TAC TGG CTG GGC AAT GAG TGC AGC CAG GAT GAG            386
Gln Tyr Asp Leu His Tyr Trp Leu Gly Asn Glu Cys Ser Gln Asp Glu
    110                 115                 120

AGC GGG GCG GCC GCC ATC TTT ACC GTG CAG CTG GAT GAC TAC CTG AAC            434
Ser Gly Ala Ala Ala Ile Phe Thr Val Gln Leu Asp Asp Tyr Leu Asn
125                 130                 135                 140

GGC CGG GCC GTG CAG CAC CGT GAG GTC CAG GGC TTC GAG TCG GCC ACC            482
Gly Arg Ala Val Gln His Arg Glu Val Gln Gly Phe Glu Ser Ala Thr
             145                 150                 155

TTC CTA GGC TAC TTC AAG TCT GGC CTG AAG TAC AAG AAA GGA GGT GTG            530
Phe Leu Gly Tyr Phe Lys Ser Gly Leu Lys Tyr Lys Lys Gly Gly Val
                 160                 165                 170
```

| | | | | | | | | | | | | | | | | |
|---|---|---|---|---|---|---|---|---|---|---|---|---|---|---|---|---|
| GCA | TCA | GGA | TTC | AAG | CAC | GTG | GTA | CCC | AAC | GAG | GTG | GTG | GTG | CAG | AGA | 578 |
| Ala | Ser | Gly | Phe | Lys | His | Val | Val | Pro | Asn | Glu | Val | Val | Val | Gln | Arg | |
| | | 175 | | | | | 180 | | | | | | 185 | | | |
| CTC | TTC | CAG | GTC | AAA | GGG | CGG | CGT | GTG | GTC | CGT | GCC | ACC | GAG | GTA | CCT | 626 |
| Leu | Phe | Gln | Val | Lys | Gly | Arg | Arg | Val | Val | Arg | Ala | Thr | Glu | Val | Pro | |
| | 190 | | | | | 195 | | | | | 200 | | | | | |
| GTG | TCC | TGG | GAG | AGC | TTC | AAC | AAT | GGC | GAC | TGC | TTC | ATC | CTG | GAC | CTG | 674 |
| Val | Ser | Trp | Glu | Ser | Phe | Asn | Asn | Gly | Asp | Cys | Phe | Ile | Leu | Asp | Leu | |
| 205 | | | | | 210 | | | | | 215 | | | | | 220 | |
| GGC | AAC | AAC | ATC | CAC | CAG | TGG | TGT | GGT | TCC | AAC | AGC | AAT | CGG | TAT | GAA | 722 |
| Gly | Asn | Asn | Ile | His | Gln | Trp | Cys | Gly | Ser | Asn | Ser | Asn | Arg | Tyr | Glu | |
| | | | | 225 | | | | | 230 | | | | | 235 | | |
| AGA | CTG | AAG | GCC | ACA | CAG | GTG | TCC | AAG | GGC | ATC | CGG | GAC | AAC | GAG | CGG | 770 |
| Arg | Leu | Lys | Ala | Thr | Gln | Val | Ser | Lys | Gly | Ile | Arg | Asp | Asn | Glu | Arg | |
| | | | 240 | | | | | 245 | | | | | 250 | | | |
| AGT | GGC | CGG | GCC | CGA | GTG | CAC | GTG | TCT | GAG | GAG | GGC | ACT | GAG | CCC | GAG | 818 |
| Ser | Gly | Arg | Ala | Arg | Val | His | Val | Ser | Glu | Glu | Gly | Thr | Glu | Pro | Glu | |
| | | 255 | | | | | 260 | | | | | 265 | | | | |
| GCG | ATG | CTC | CAG | GTG | CTG | GGC | CCC | AAG | CCG | GCT | CTG | CCT | GCA | GGT | ACC | 866 |
| Ala | Met | Leu | Gln | Val | Leu | Gly | Pro | Lys | Pro | Ala | Leu | Pro | Ala | Gly | Thr | |
| | 270 | | | | | 275 | | | | | 280 | | | | | |
| GAG | GAC | ACC | GCC | AAG | GAG | GAT | GCG | GCC | AAC | CGC | AAG | CTG | GCC | AAG | CTC | 914 |
| Glu | Asp | Thr | Ala | Lys | Glu | Asp | Ala | Ala | Asn | Arg | Lys | Leu | Ala | Lys | Leu | |
| 285 | | | | | 290 | | | | | 295 | | | | | 300 | |
| TAC | AAG | GTC | TCC | AAT | GGT | GCA | GGG | ACC | ATG | TCC | GTC | TCC | CTC | GTG | GCT | 962 |
| Tyr | Lys | Val | Ser | Asn | Gly | Ala | Gly | Thr | Met | Ser | Val | Ser | Leu | Val | Ala | |
| | | | | 305 | | | | | 310 | | | | | 315 | | |
| GAT | GAG | AAC | CCC | TTC | GCC | CAG | GGG | GCC | CTG | AAG | TCA | GAG | GAC | TGC | TTC | 1010 |
| Asp | Glu | Asn | Pro | Phe | Ala | Gln | Gly | Ala | Leu | Lys | Ser | Glu | Asp | Cys | Phe | |
| | | | 320 | | | | | 325 | | | | | 330 | | | |
| ATC | CTG | GAC | CAC | GGC | AAA | GAT | GGG | AAA | ATC | TTT | GTC | TGG | AAA | GGC | AAG | 1058 |
| Ile | Leu | Asp | His | Gly | Lys | Asp | Gly | Lys | Ile | Phe | Val | Trp | Lys | Gly | Lys | |
| | | 335 | | | | | 340 | | | | | 345 | | | | |
| CAG | GCA | AAC | ACG | GAG | GAG | AGG | AAG | GCT | GCC | CTC | AAA | ACA | GCC | TCT | GAC | 1106 |
| Gln | Ala | Asn | Thr | Glu | Glu | Arg | Lys | Ala | Ala | Leu | Lys | Thr | Ala | Ser | Asp | |
| | 350 | | | | | 355 | | | | | 360 | | | | | |
| TTC | ATC | ACC | AAG | ATG | GAC | TAC | CCC | AAG | CAG | ACT | CAG | GTC | TCG | GTC | CTT | 1154 |
| Phe | Ile | Thr | Lys | Met | Asp | Tyr | Pro | Lys | Gln | Thr | Gln | Val | Ser | Val | Leu | |
| 365 | | | | | 370 | | | | | 375 | | | | | 380 | |
| CCT | GAG | GGC | GGT | GAG | ACC | CCA | CTG | TTC | AAG | CAG | TTC | TTC | AAG | AAC | TGG | 1202 |
| Pro | Glu | Gly | Gly | Glu | Thr | Pro | Leu | Phe | Lys | Gln | Phe | Phe | Lys | Asn | Trp | |
| | | | | 385 | | | | | 390 | | | | | 395 | | |
| CGG | GAC | CCA | GAC | CAG | ACA | GAT | GGC | CTG | GGC | TTG | TCC | TAC | CTT | TCC | AGC | 1250 |
| Arg | Asp | Pro | Asp | Gln | Thr | Asp | Gly | Leu | Gly | Leu | Ser | Tyr | Leu | Ser | Ser | |
| | | | 400 | | | | | 405 | | | | | 410 | | | |
| CAT | ATC | GCC | AAC | GTG | GAG | CGG | GTG | CCC | TTC | GAC | GCC | GCC | ACC | CTG | CAC | 1298 |
| His | Ile | Ala | Asn | Val | Glu | Arg | Val | Pro | Phe | Asp | Ala | Ala | Thr | Leu | His | |
| | | 415 | | | | | 420 | | | | | 425 | | | | |
| ACC | TCC | ACT | GCC | ATG | GCC | GCC | CAG | CAC | GGC | ATG | GAT | GAC | GAT | GGC | ACA | 1346 |
| Thr | Ser | Thr | Ala | Met | Ala | Ala | Gln | His | Gly | Met | Asp | Asp | Asp | Gly | Thr | |
| | 430 | | | | | 435 | | | | | 440 | | | | | |
| GGC | CAG | AAA | CAG | ATC | TGG | AGA | ATC | GAA | GGT | TCC | AAC | AAG | GTG | CCC | GTG | 1394 |
| Gly | Gln | Lys | Gln | Ile | Trp | Arg | Ile | Glu | Gly | Ser | Asn | Lys | Val | Pro | Val | |
| 445 | | | | | 450 | | | | | 455 | | | | | 460 | |
| GAC | CCT | GCC | ACA | TAT | GGA | CAG | TTC | TAT | GGA | GGC | GAC | AGC | TAC | ATC | ATT | 1442 |
| Asp | Pro | Ala | Thr | Tyr | Gly | Gln | Phe | Tyr | Gly | Gly | Asp | Ser | Tyr | Ile | Ile | |
| | | | | 465 | | | | | 470 | | | | | 475 | | |
| CTG | TAC | AAC | TAC | CGC | CAT | GGT | GGC | CGC | CAG | GGG | CAG | ATA | ATC | TAT | AAC | 1490 |
| Leu | Tyr | Asn | Tyr | Arg | His | Gly | Gly | Arg | Gln | Gly | Gln | Ile | Ile | Tyr | Asn | |
| | | | | 480 | | | | | 485 | | | | | 490 | | |
| TGG | CAG | GGT | GCC | CAG | TCT | ACC | CAG | GAT | GAG | GTC | GCT | GCA | TCT | GCC | ATC | 1538 |
| Trp | Gln | Gly | Ala | Gln | Ser | Thr | Gln | Asp | Glu | Val | Ala | Ala | Ser | Ala | Ile | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     | 495 |     |     |     |     | 500 |     |     |     |     |     | 505 |     |     |     |      |
| CTG | ACT | GCT | CAG | CTG | GAT | GAG | GAG | CTG | GGA | GGT | ACC | CCT | GTC | CAG | AGC | 1586 |
| Leu | Thr | Ala | Gln | Leu | Asp | Glu | Glu | Leu | Gly | Gly | Thr | Pro | Val | Gln | Ser |      |
|     | 510 |     |     |     |     | 515 |     |     |     |     |     | 520 |     |     |     |      |
| CGT | GTG | GTC | CAA | GGC | AAG | GAG | CCC | GCC | CAC | CTC | ATG | AGC | CTG | TTT | GGT | 1634 |
| Arg | Val | Val | Gln | Gly | Lys | Glu | Pro | Ala | His | Leu | Met | Ser | Leu | Phe | Gly |      |
| 525 |     |     |     |     | 530 |     |     |     |     | 535 |     |     |     |     | 540 |      |
| GGG | AAG | CCC | ATG | ATC | ATC | TAC | AAG | GGC | GGC | ACC | TCC | CGC | GAG | GGC | GGG | 1682 |
| Gly | Lys | Pro | Met | Ile | Ile | Tyr | Lys | Gly | Gly | Thr | Ser | Arg | Glu | Gly | Gly |      |
|     |     |     |     | 545 |     |     |     |     | 550 |     |     |     |     | 555 |     |      |
| CAG | ACA | GCC | CCT | GCC | AGC | ACC | CGC | CTC | TTC | CAG | GTC | CGC | GCC | AAC | AGC | 1730 |
| Gln | Thr | Ala | Pro | Ala | Ser | Thr | Arg | Leu | Phe | Gln | Val | Arg | Ala | Asn | Ser |      |
|     |     |     | 560 |     |     |     |     | 565 |     |     |     |     | 570 |     |     |      |
| GCT | GGA | GCC | ACC | CGG | GCT | GTT | GAG | GTA | TTG | CCT | AAG | GCT | GGT | GCA | CTG | 1778 |
| Ala | Gly | Ala | Thr | Arg | Ala | Val | Glu | Val | Leu | Pro | Lys | Ala | Gly | Ala | Leu |      |
|     |     | 575 |     |     |     |     | 580 |     |     |     |     | 585 |     |     |     |      |
| AAC | TCC | AAC | GAT | GCC | TTT | GTT | CTG | AAA | ACC | CCC | TCA | GCC | GCC | TAC | CTG | 1826 |
| Asn | Ser | Asn | Asp | Ala | Phe | Val | Leu | Lys | Thr | Pro | Ser | Ala | Ala | Tyr | Leu |      |
|     | 590 |     |     |     |     | 595 |     |     |     |     | 600 |     |     |     |     |      |
| TGG | GTG | GGT | ACA | GGA | GCC | AGC | GAG | GCA | GAG | AAG | ACG | GGG | GCC | CAG | GAG | 1874 |
| Trp | Val | Gly | Thr | Gly | Ala | Ser | Glu | Ala | Glu | Lys | Thr | Gly | Ala | Gln | Glu |      |
| 605 |     |     |     |     | 610 |     |     |     |     | 615 |     |     |     |     | 620 |      |
| CTG | CTC | AGG | GTG | CTG | CGG | GCC | CAA | CCT | GTG | CAG | GTG | GCA | GAA | GGC | AGC | 1922 |
| Leu | Leu | Arg | Val | Leu | Arg | Ala | Gln | Pro | Val | Gln | Val | Ala | Glu | Gly | Ser |      |
|     |     |     |     | 625 |     |     |     |     | 630 |     |     |     |     | 635 |     |      |
| GAG | CCA | GAT | GGC | TTC | TGG | GAG | GCC | CTG | GGC | GGG | AAG | GCT | GCC | TAC | CGC | 1970 |
| Glu | Pro | Asp | Gly | Phe | Trp | Glu | Ala | Leu | Gly | Gly | Lys | Ala | Ala | Tyr | Arg |      |
|     |     |     | 640 |     |     |     |     | 645 |     |     |     |     | 650 |     |     |      |
| ACA | TCC | CCA | CGG | CTG | AAG | GAC | AAG | AAG | ATG | GAT | GCC | CAT | CCT | CCT | CGC | 2018 |
| Thr | Ser | Pro | Arg | Leu | Lys | Asp | Lys | Lys | Met | Asp | Ala | His | Pro | Pro | Arg |      |
|     |     | 655 |     |     |     |     | 660 |     |     |     |     | 665 |     |     |     |      |
| CTC | TTT | GCC | TGC | TCC | AAC | AAG | ATT | GGA | CGT | TTT | GTG | ATC | GAA | GAG | GTT | 2066 |
| Leu | Phe | Ala | Cys | Ser | Asn | Lys | Ile | Gly | Arg | Phe | Val | Ile | Glu | Glu | Val |      |
|     | 670 |     |     |     |     | 675 |     |     |     |     | 680 |     |     |     |     |      |
| CCT | GGT | GAG | CTC | ATG | CAG | GAA | GAC | CTG | GCA | ACG | GAT | GAC | GTC | ATG | CTT | 2114 |
| Pro | Gly | Glu | Leu | Met | Gln | Glu | Asp | Leu | Ala | Thr | Asp | Asp | Val | Met | Leu |      |
| 685 |     |     |     |     | 690 |     |     |     |     | 695 |     |     |     |     | 700 |      |
| CTG | GAC | ACC | TGG | GAC | CAG | GTC | TTT | GTC | TGG | GTT | GGA | AAG | GAT | TCT | CAA | 2162 |
| Leu | Asp | Thr | Trp | Asp | Gln | Val | Phe | Val | Trp | Val | Gly | Lys | Asp | Ser | Gln |      |
|     |     |     |     | 705 |     |     |     |     | 710 |     |     |     |     | 715 |     |      |
| GAA | GAA | GAA | AAG | ACA | GAA | GCC | TTG | ACT | TCT | GCT | AAG | CGG | TAC | ATC | GAG | 2210 |
| Glu | Glu | Glu | Lys | Thr | Glu | Ala | Leu | Thr | Ser | Ala | Lys | Arg | Tyr | Ile | Glu |      |
|     |     |     | 720 |     |     |     |     | 725 |     |     |     |     | 730 |     |     |      |
| ACG | GAC | CCA | GCC | AAT | CGG | GAT | CGG | CGG | ACG | CCC | ATC | ACC | GTG | GTG | AAG | 2258 |
| Thr | Asp | Pro | Ala | Asn | Arg | Asp | Arg | Arg | Thr | Pro | Ile | Thr | Val | Val | Lys |      |
|     |     | 735 |     |     |     |     | 740 |     |     |     |     | 745 |     |     |     |      |
| CAA | GGC | TTT | GAG | CCT | CCC | TCC | TTT | GTG | GGC | TGG | TTC | CTT | GGC | TGG | GAT | 2306 |
| Gln | Gly | Phe | Glu | Pro | Pro | Ser | Phe | Val | Gly | Trp | Phe | Leu | Gly | Trp | Asp |      |
|     | 750 |     |     |     |     | 755 |     |     |     |     | 760 |     |     |     |     |      |
| GAT | GAT | TAC | TGG | TCT | GTG | GAC | CCC | TTG | GAC | AGG | GCC | ATG | GCT | GAG | CTG | 2354 |
| Asp | Asp | Tyr | Trp | Ser | Val | Asp | Pro | Leu | Asp | Arg | Ala | Met | Ala | Glu | Leu |      |
| 765 |     |     |     |     | 770 |     |     |     |     | 775 |     |     |     |     | 780 |      |
| GCT | GCC | TGAGGAGGGG | CAGGGCCCAC | CCATGTCACC | GGTCAGTGCC | TTTTGGAACT | | | | | | | | | | 2410 |
| Ala | Ala |     |     |     |     |     |     |     |     |     |     |     |     |     |     |      |
| GTCCTTCCCT | CAAAGAGGCC | TTAGAGCGAG | CAGAGCAGCT | CTGCTATGAG | TGTGTGTGTG | | | | | | | | | | | 2470 |
| TGTGTGTGTT | GTTTCTTTTT | TTTTTTTTA | CAGTATCCAA | AAATAGCCCT | GCAAAAATTC | | | | | | | | | | | 2530 |
| AGAGTCCTTG | CAAAATTGTC | TAAAATGTCA | GTGTTTGGGA | AATTAAATCC | AATAAAAACA | | | | | | | | | | | 2590 |
| TTTTGAAGTG | TGAAAAAA   |     |     |     |     |     |     |     |     |     |     |     |     |     |     | 2608 |

( 2 ) INFORMATION FOR SEQ ID NO:2:

( i ) SEQUENCE CHARACTERISTICS:
        ( A ) LENGTH: 782 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Pro His Arg Pro Ala Pro Ala Leu Leu Cys Ala Leu Ser Leu
 1               5                  10                  15
Ala Leu Cys Ala Leu Ser Leu Pro Val Arg Ala Ala Thr Ala Ser Arg
                20                  25                  30
Gly Ala Ser Gln Ala Gly Ala Pro Gln Gly Arg Val Pro Glu Ala Arg
            35                  40                  45
Pro Asn Ser Met Val Val Glu His Pro Glu Phe Leu Lys Ala Gly Lys
        50                  55                  60
Glu Pro Gly Leu Gln Ile Trp Arg Val Glu Lys Phe Asp Leu Val Pro
 65                  70                  75                  80
Val Pro Thr Asn Leu Tyr Gly Asp Phe Phe Thr Gly Asp Ala Tyr Val
                85                  90                  95
Ile Leu Lys Thr Val Gln Leu Arg Asn Gly Asn Leu Gln Tyr Asp Leu
                100                 105                 110
His Tyr Trp Leu Gly Asn Glu Cys Ser Gln Asp Glu Ser Gly Ala Ala
            115                 120                 125
Ala Ile Phe Thr Val Gln Leu Asp Asp Tyr Leu Asn Gly Arg Ala Val
        130                 135                 140
Gln His Arg Glu Val Gln Gly Phe Glu Ser Ala Thr Phe Leu Gly Tyr
145                 150                 155                 160
Phe Lys Ser Gly Leu Lys Tyr Lys Lys Gly Gly Val Ala Ser Gly Phe
                165                 170                 175
Lys His Val Val Pro Asn Glu Val Val Val Gln Arg Leu Phe Gln Val
                180                 185                 190
Lys Gly Arg Arg Val Val Arg Ala Thr Glu Val Pro Val Ser Trp Glu
            195                 200                 205
Ser Phe Asn Asn Gly Asp Cys Phe Ile Leu Asp Leu Gly Asn Asn Ile
        210                 215                 220
His Gln Trp Cys Gly Ser Asn Ser Asn Arg Tyr Glu Arg Leu Lys Ala
225                 230                 235                 240
Thr Gln Val Ser Lys Gly Ile Arg Asp Asn Glu Arg Ser Gly Arg Ala
                245                 250                 255
Arg Val His Val Ser Glu Glu Gly Thr Glu Pro Glu Ala Met Leu Gln
                260                 265                 270
Val Leu Gly Pro Lys Pro Ala Leu Pro Ala Gly Thr Glu Asp Thr Ala
            275                 280                 285
Lys Glu Asp Ala Ala Asn Arg Lys Leu Ala Lys Leu Tyr Lys Val Ser
        290                 295                 300
Asn Gly Ala Gly Thr Met Ser Val Ser Leu Val Ala Asp Glu Asn Pro
305                 310                 315                 320
Phe Ala Gln Gly Ala Leu Lys Ser Glu Asp Cys Phe Ile Leu Asp His
                325                 330                 335
Gly Lys Asp Gly Lys Ile Phe Val Trp Lys Gly Lys Gln Ala Asn Thr
            340                 345                 350
Glu Glu Arg Lys Ala Ala Leu Lys Thr Ala Ser Asp Phe Ile Thr Lys
        355                 360                 365
Met Asp Tyr Pro Lys Gln Thr Gln Val Ser Val Leu Pro Glu Gly Gly
370                 375                 380
```

| | | | | | | | | | | | | | | |
|---|---|---|---|---|---|---|---|---|---|---|---|---|---|---|
| Glu | Thr | Pro | Leu | Phe | Lys | Gln | Phe | Phe | Lys | Asn | Trp | Arg | Asp | Pro | Asp |
| 385 | | | | | 390 | | | | 395 | | | | | | 400 |
| Gln | Thr | Asp | Gly | Leu | Gly | Leu | Ser | Tyr | Leu | Ser | Ser | His | Ile | Ala | Asn |
| | | | | 405 | | | | | 410 | | | | | 415 | |
| Val | Glu | Arg | Val | Pro | Phe | Asp | Ala | Ala | Thr | Leu | His | Thr | Ser | Thr | Ala |
| | | | 420 | | | | | 425 | | | | | 430 | | |
| Met | Ala | Ala | Gln | His | Gly | Met | Asp | Asp | Asp | Gly | Thr | Gly | Gln | Lys | Gln |
| | | 435 | | | | | 440 | | | | | 445 | | | |
| Ile | Trp | Arg | Ile | Glu | Gly | Ser | Asn | Lys | Val | Pro | Val | Asp | Pro | Ala | Thr |
| | 450 | | | | | 455 | | | | | 460 | | | | |
| Tyr | Gly | Gln | Phe | Tyr | Gly | Gly | Asp | Ser | Tyr | Ile | Ile | Leu | Tyr | Asn | Tyr |
| 465 | | | | | 470 | | | | 475 | | | | | | 480 |
| Arg | His | Gly | Gly | Arg | Gln | Gly | Gln | Ile | Ile | Tyr | Asn | Trp | Gln | Gly | Ala |
| | | | | 485 | | | | | 490 | | | | | 495 | |
| Gln | Ser | Thr | Gln | Asp | Glu | Val | Ala | Ala | Ser | Ala | Ile | Leu | Thr | Ala | Gln |
| | | | 500 | | | | | 505 | | | | | 510 | | |
| Leu | Asp | Glu | Glu | Leu | Gly | Gly | Thr | Pro | Val | Gln | Ser | Arg | Val | Val | Gln |
| | | 515 | | | | | 520 | | | | | 525 | | | |
| Gly | Lys | Glu | Pro | Ala | His | Leu | Met | Ser | Leu | Phe | Gly | Gly | Lys | Pro | Met |
| | 530 | | | | | 535 | | | | | 540 | | | | |
| Ile | Ile | Tyr | Lys | Gly | Gly | Thr | Ser | Arg | Glu | Gly | Gly | Gln | Thr | Ala | Pro |
| 545 | | | | | 550 | | | | | 555 | | | | | 560 |
| Ala | Ser | Thr | Arg | Leu | Phe | Gln | Val | Arg | Ala | Asn | Ser | Ala | Gly | Ala | Thr |
| | | | | 565 | | | | | 570 | | | | | 575 | |
| Arg | Ala | Val | Glu | Val | Leu | Pro | Lys | Ala | Gly | Ala | Met | Asn | Ser | Asn | Asp |
| | | | 580 | | | | | 585 | | | | | 590 | | |
| Ala | Phe | Val | Leu | Lys | Thr | Pro | Ser | Ala | Ala | Tyr | Leu | Trp | Val | Gly | Thr |
| | | 595 | | | | | 600 | | | | | 605 | | | |
| Gly | Ala | Ser | Glu | Ala | Glu | Lys | Thr | Gly | Ala | Gln | Glu | Leu | Leu | Arg | Val |
| | 610 | | | | | 615 | | | | | 620 | | | | |
| Leu | Arg | Ala | Gln | Pro | Val | Gln | Val | Ala | Glu | Gly | Ser | Glu | Pro | Asp | Gly |
| 625 | | | | | 630 | | | | | 635 | | | | | 640 |
| Phe | Trp | Glu | Ala | Leu | Gly | Gly | Lys | Ala | Ala | Tyr | Arg | Thr | Ser | Pro | Arg |
| | | | | 645 | | | | | 650 | | | | | 655 | |
| Leu | Lys | Asp | Lys | Lys | Met | Asp | Ala | His | Pro | Pro | Arg | Leu | Phe | Ala | Cys |
| | | | 660 | | | | | 665 | | | | | 670 | | |
| Ser | Asn | Lys | Ile | Gly | Arg | Phe | Val | Ile | Glu | Glu | Val | Pro | Gly | Glu | Leu |
| | | 675 | | | | | 680 | | | | | 685 | | | |
| Met | Gln | Glu | Asp | Leu | Ala | Thr | Asp | Asp | Val | Met | Leu | Leu | Asp | Thr | Trp |
| | 690 | | | | | 695 | | | | | 700 | | | | |
| Asp | Gln | Val | Phe | Val | Trp | Val | Gly | Lys | Asp | Ser | Gln | Glu | Glu | Glu | Lys |
| 705 | | | | | 710 | | | | | 715 | | | | | 720 |
| Thr | Glu | Ala | Leu | Thr | Ser | Ala | Lys | Arg | Tyr | Ile | Glu | Thr | Asp | Pro | Ala |
| | | | | 725 | | | | | 730 | | | | | 735 | |
| Asn | Arg | Asp | Arg | Arg | Thr | Pro | Ile | Thr | Val | Val | Lys | Gln | Gly | Phe | Glu |
| | | | 740 | | | | | 745 | | | | | 750 | | |
| Pro | Pro | Ser | Phe | Val | Gly | Trp | Phe | Leu | Gly | Trp | Asp | Asp | Asp | Tyr | Trp |
| | | 755 | | | | | 760 | | | | | 765 | | | |
| Ser | Val | Asp | Pro | Leu | Asp | Arg | Ala | Met | Ala | Glu | Leu | Ala | Ala | | |
| | 770 | | | | | 775 | | | | | 780 | | | | |

GENETIC DIAGNOSIS OF TORSION DYSTONIA

This invention was made with Government support; the Government has certain rights in this invention.

This application is a continuation-in-part application of U.S. application Ser. No. 07/353,432, filed May 18, 1989, now abandoned, whose disclosure is herein incorporated in its entirety.

FIELD OF THE INVENTION

The invention relates to a detection test, especially a presymptomatic test, for torsion dystonia, which uses recombinant DNA techniques in genetic linkage analysis.

BACKGROUND OF THE INVENTION

Torsion dystonia is a movement disorder of unknown etiology characterized by sustained muscle contractions, frequently causing twisted and repetitive movements, or abnormal postures (Fahn, S., *In Movement Disorders* 2, C. D. Marsden, and S. Fahn, eds. (Boston: Butterworths), pp. 332-358 (1987)). Other symptoms include spastic torticollis, blepharospasm, writer's cramp, dysphonia, tremor and stuttering. About 66% of cases presenting with predominantly dystonic symptoms appear to be primary (idiopathic), with the remainder resulting as secondary symptoms of other neurologic disorders, such as $GM_2$ gangliosidosis, Hallervorden Spatz, Parkinson disease, Huntington disease (ibid.) and Leber disease (Novotny, E. J. et al., *Neurol.* 36:1053-1060 (1986)), or the result of drug treatment or brain lesions, especially in the region of the basal ganglia. The disease frequency of idiopathic torsion dystonia (ITD) is unknown and probably underestimated, because the; disease is variable in its expression and some affected individuals do not come to medical attention. There are about 100,000 cases of dystonia in the United States, about half of which are thought to be hereditary. Disease frequency has been roughly estimated at 1/160,000 in the general population (Zeman, W. et al., *Psychiatric Neurologia Neurochirurgia* 77-121 (1967)) with a much higher frequency of 1/15,000-1/23,000 in Ashkenazi Jews (Zilber, N. et al., *J. Med. Genet.* 21:13-20 (1984); Eldridge, R., *Neurol.* 20:1-78 (1970)).

Different clinical subtypes of hereditary dystonia have been described in the general population based on age-of-onset, type of dystonic symptoms, and responsiveness to drugs (Segawa, M. et al., *Adv. Neurol.* 14:215-233 (1976); Lance, J. W., *Annal. Neurol.* 2:285-293 (1977); Quinn, N. P. et al., *Adv. Neurol.* 50:391-401 (1988); Kurlan, R. et al., *Adv. Neurol.* 50:385-389 (1988); Nygaard, T. G. et al., *Adv. Neurol.* 50:377-384 (1988); Forsgren, L. et al., *Adv. Neurol.* 50:83-92 (1988)). Almost all familial forms appear to follow an autosomal dominant mode of inheritance with reduced penetrance, with the exception being an X-linked Filipino form (Lee, L. V. et al., *Adv. Neurol.* 14:137-151 (1976); Fahn, S. et al., *Ann. Neurol.* 24:179 (1988)). In the Jewish, as well as some non-Jewish, populations cases with early onset cluster at age: 9 years and tend to progress to more generalized involvement, while cases with later onset cluster around age 48 years and tend to manifest signs of more restricted regions (Fahn, S., *Clinical Neuropharm.* 9 (Suppl. 2):S37-S48 (1986)). However, age-of-onset and clinical expressivity can vary remarkably within a family where presumably all cases have the same defective gene. Recent studies support an autosomal dominant mode of inheritance in the Jewish population with a penetrance of 31% (Bressman, S. B. et al., *Adv. Neurol.* 50:45-56 (1988b); Zilber, N. et al., *J. Med. Genet.* 21:13-20 (1984)), although earlier studies suggested an autosomal recessive mode of inheritance in some families (Eldridge, R., *Neurol.* 20:1-78 (1970)).

Dystonia in the Jewish population is a particularly important medical problem because of the presumed high frequency (1/10,000) of this apparently dominant allele (Zilber, N. et al., *J. Med. Genet.* 21:13-20 (1984)); the low penetrance of the allele which masks carrier status; and the usually early age of onset, which is associated with a more severe course of the illness (Fahn, S., *Clinical Neuropharm.* 9(Suppl. 2):S37-S48 (1986)). The similarity in clinical features and age of onset between dystonia in the Jewish and non-Jewish populations (Burke, R. E. et al., *Movement Disorders* 1:163-178 (1986); Brin, M. F. et al., *Neurol.* 37:137 (1987); Burke, R. E. et al., *Neurol.*, (1989)), including the non-Jewish family studied here, suggests the possibility that the same gene is involved.

The molecular etiology of hereditary dystonia has been difficult to understand as only a limited number of neurochemical and neuropathological studies have been carried out on brain samples of deceased patients, and these patients have fallen into both hereditary and non-hereditary types of dystonia. The fact that a number of different types of lesions in the basal ganglia can cause dystonia serves to implicate this area of the brain, which is known to control involuntary movements (Calne, D. B. et al., *Adv. Neurol.* 50:9-33 (1988); Marsden, C. D. et al., *Brain* 108:461-483 (1985)). In addition, over 24 different hereditary conditions can manifest secondary dystonic symptoms (Fahn, S., *In Movement Disorders* 2, C. D. Marsden, and S. Fahn, eds. (Boston: Butterworths), pp. 332-358 (1987)). Together these findings suggest that dystonic symptoms can be elicited fairly specifically in rats by stereotactic injection of the N-terminal end of pro-opiomelanocortin into the locus coeruleus (Jacquet, Y. F. et al., *Science* 218:175-177 (1982)) or norepinephrine into the striatum, red nucleus, accumbens or thalamus (de Yebenes, J. G. et al., *Neurol.* 38(Suppl 1):207 (1988)). Recently, discrete neuropathologic changes, including neurofibrillary tangles, have been observed in the brain of a 29-year-old Jewish male (Hedreen, J. C. et al., *Adv. Neurol.* 50:123-130 (1988)); previous studies found no abnormalities in two cases of hereditary dystonia (Zeman, W., *Neurol.* 20(Part II):79-88 (1970)). Drug treatments that can induce dystonia symptoms in humans include L-DOPA, D-2 receptor antagonists and anticonvulsants (Fahn, S., *In Movement Disorders* 2, C. D. Marsden, and S. Fahn, eds. (Boston: Butterworths), pp. 332-358 (1987)). In some patients, drug treatment can alleviate symptoms, but in most forms of dystonia there is no consistent "best" treatment. Drugs which have proven useful in some patients include the anticholinergics, benzodiazepines and carbamazepine. Two potentially etiologically and genetically distinct forms of hereditary dystonia that do respond to specific pharmacotherapy are the dystonia-Parkinsonism complex which can be treated with levodopa (Nygaard, T. G. et al., *Adv. Neurol.* 50:377-384 (1988)), and myoclonic-dystonia which can be relieved by alcohol (Quinn, N. P. et aL, *Adv. Neurol.* 50:391-401 (1988)).

Linkage analysis using DNA polymorphisms provides a powerful means to find the chromosomal location of genes causing hereditary diseases in the human population when appropriate family material is available. Recent advances in this analysis include highly polymorphic markers conferred by variable number tandem repeat (VNTR) sequences scattered throughout the genome (Nakamura, Y. et al., *Science* 235:1616-1622 (1987); Jeffreys, A. J. et al., *Nature* 314:67-73 (1985)), and a large number of marker sequences spaced at known recombination intervals spanning essentially the entire human genome at $\leq 5$ centiMorgan (cM) intervals (Donis-Keller, H. et al., *Cell* 51:319-337 (1987); White, R. et al., *Nature* 313:101-105 (1985)). Using this approach the chromosomal locations of over 20 genes causing hereditary neurologic diseases have been established (see HHMI, Human Gene Mapping Library). For two of these diseases for which deletional mutations exist, retinoblastoma and Duchenne muscular dystrophy, this tocational information led to the discovery of the responsible gene, which in both cases encoded a previously undescribed protein (Lee, W. H. et al., *Nature* 329:642-645. (1987); Hoffman, E. P. et al., *Cell* 51:919-928 (1987)).

Until the present invention, the chromosomal location of the gene(s) causing torsion dystonia has not yet been identified. Using protein and restriction fragment length polymorphic (RFLP) markers, studies in a large non-Jewish family of French, English and American Indian descent, originally described by Johnson et al. (*Arch. Neurol.* 7:301-313 (1962)), excluded about 20% of the autosomal complement of the genome (Kramer, P. L. et al., *Adv. Neurol.* 50:57-66 (1988); Falk, C. T. et al., *Adv. Neurol.* 50:67-72 (1988)), including large regions of chromosomes 11p, 13q and 21q (Kramer, P. L. et al., *Genet. Epidemiol.* 4:377-386 (1987)), and the candidate genes pro-opimelanocortin and glutamic acid decarboxylase (Breakefield, X. O. et al., *J. Neurogenet.* 3:159.-175 (1986)). This family exhibits a form of dystonia which is consistent with an autosomal dominant mode of inheritance with reduced penetrance. The clinical syndrome and age-of-onset of dystonia in this family resemble that described for Jewish and non-Jewish families with pedigrees consistent with dominant inheritance (Burke, R. E. et al., *Movement Disorders* 1:163-178 (1986); Brin, M. F. et al., Neurol. 37:137 (1987); Burke, R. E. et al., *Neurol.*, (1989)).

Research on the molecular etiology of dystonia has been confounded by the large number of hereditary and environmental factors that can produce dystonic symptoms and by the paucity of neuropathological and neurochemical studies on brains from affected individuals. The finding of a linked marker for one hereditary form of dystonia will help to resolve the number of different genes underlying hereditary dystonias. These markers can be used eventually to provide genetic counseling in some affected families. Most importantly, the delineation of the genomic region containing the dystonia gene will provide a means to eventually discover and characterize this gene and its encoded protein. The finding of linked markers will also make it possible to evaluate the role of gene(s) in this chromosomal region in other forms of hereditary dystonia, (Eldridge, R., *Neurol.* 20:1-78 (1970)), Swedish with late onset (Forsgren, L. et al., *Adv. Neurol.* 50:83-92 (1988)), dopa-responsive with features of Parkinsonism (Nygaard, T. G. et al., *Adv. Neurol.* 50:377-384 (1988)), paroxysmal (Bressman, S. B. et al., *Adv. Neurol.* 50:403-413 (1988a)), myoclonic-dystonia (Quinn, N. P. et al., *Adv. Neurol.* 50:391-401 (1988); Kurlan, R. et al., *Adv. Neurol.* 50:385-389 (1988)) and dystonia with diurnal fluctuations (Segawa, M. et al., *Adv. Neurol.* 14:215-233 (1976)).

SUMMARY OF THE INVENTION

The invention is drawn to the diagnosis of idiopathic torsion dystonia (ITD). The involvement of the dystonia gene on 9q and two forms of hereditary dystonia with early onset has been confirmed and the chromosomal location of the gene (DYT1) has been defined. In particular, the region on chromosome 9q34 containing a dystonia gene has been localized to a 2 cM region between loci AK1 and ASS in Jewish families. Furthermore, a region on chromosome 11, 11q, has been implicated as associated with torsion dystonia. Specifically, the 11q22-q23 region has been implicated as bearing the disease gene in an American family with myoclonic dystonia.

Methods for allele association, or linkage disequilibrium, are provided to determine the propensity of an individual for developing dystonia. Additionally, DNA probes or markers are provided for mapping the appropriate regions involved in torsion dystonia. The invention also finds use in determining environmental and other genetic factors related to the development of torsion dystonia.

DEFINITIONS

Figure 1:
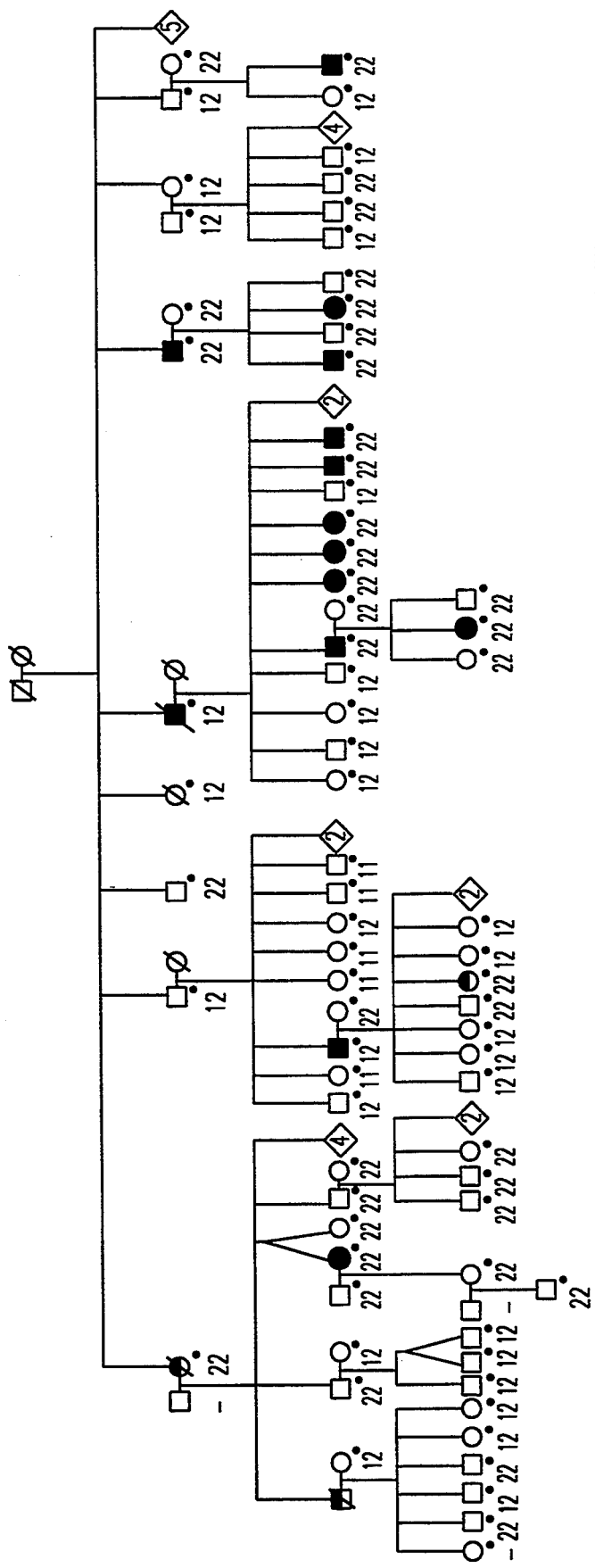
FIG. 1 shows the pedigree of family with dystonia. All individuals with a dot received a rigorous neurologic evaluation through the Dystonia Clinical Research Center at Columbia University. The oldest male was deemed affected on the basis of history (Johnson, W. et al., *Arch. Neurol.* 7:301-313 (1962)). Open symbols=unaffected and possible affected; solid symbols=affected; half-solid symbols=probable affected. The allelic status of individuals at the gelsolin (GSN) locus is indicated numerically below the symbols.

A number of technical terms and expressions are used throughout the specification and claims. In order to assure uniformity and avoid ambiguity the following definitions are provided.

"Linked Genes." Genes that are "linked" have their loci within measurable distances of one another on the same chromosome.

"Linkage Analysis." Linkage analysis provide. s a means for determining the frequency with which a particular disease state cosegregates with alleles at genetic "marker" loci, thereby determining whether the gene causing the disorder is close to the marker. The basic idea of linkage analysis is that the closer together two genes are on a particular chromosome the less likely it is that a crossover between them a recombination event—will occur during meiosis.

"Recombination." The formation of new combinations of linked genes by crossing over between their loci.

"Map Unit." A measure of distance between two loci on a chromosome based on the percentage frequency of recombination between them; one map unit is equivalent to one centimorgan (cM) or one recombination per 100 helioses.

"Genetic Marker." A genetic marker is a trait used in studies of families and populations that is genetically determined, can be accurately classified, has a simple unequivocal pattern of inheritance and has heritable variations common enough to allow it to be chssified as genetic polymorphism.

"Recombination Frequency." The recombination frequency is a measure of the average amount of recombination between two genetic loci and can be used to as a measure of the relative distance between two gene loci in constructing linkage maps.

"Lod score method." The term "lod" is an abbreviation of "logarithm of the odds." The lod score method was developed by Morton (Morton, N. E., *Am. J. Hum Genet.* 7:277–318 (1955)) and is a method of determining linkage in humans where the linkage phase may be unknown (i.e., when it is not known if the genes are on the same or different chromosomes). The method was extended by Elston et al. (*Hum. Hered.* 21:523–542 (1971)) and was incorporated into the computer program LIPED by Ott (Ott, J., *Analysis of Human Genetic Linkage*, The Johns Hopkins University Press, Baltimore, 1976). The principle is to set up a series of theoretical recombination frequencies and for each theoretical value calculate the relative odds Z for a particular pedigree on the basis of that recombination fraction, as compared with the likelihood of there being no linkage. If the theoretical recombination frequency, $\theta = 0.0$, there is absolute linkage. If $\theta = 0.50$, there is no linkage. $Z(\theta) = \log_{10}$ [(Probability of family for $\theta = 0.01$, etc.) / (Probability of family for $\theta = 0.50$)]. The ratio is expressed as a logarithm. A lod score of 3 (equivalent to a 1000:1 probability in favor of linkage) is arbitrarily accepted as proof of linkage, and a score of $-2$ is taken to rule out linkage.

"p." (1) The short arm of a chromosome is the "p" arm (from the French "petit"). (2) In population genetics, p is often also used to indicate the frequency of the more common allele of a pair.

"q." (1) The long arm of a chromosome is the "q" arm. (2) In population genetics, "q" is often also used to indicate the frequency of the rarer allele of a pair.

"Pedigree." A pedigree is a shorthand method of classifying the genetic data from a family on a chart using symbols. For example, a male is usually denoted by a square, female by a circle, and person of unspecified sex by a diamond. A slash through a symbol means the person has died. A symbol which is filled in means the person is afflicted with the disease in question. A symbol partially filled in means the person is heterozygous for the autosomal recessive disease gene. A symbol with a number in it indicates the number of children of that sex.

"Heterozygote and Homozygote." An individual who has two different alleles, at a given locus on a pair of homologous chromosomes is a heterozygote for that locus. An individual who has two identical alleles at a given locus on a pair of homologous chromosomes is a homozygote for that locus.

"Polymorphism." The occurrence together in a population of two or more genetically determined alternative genotypes. Arbitrarily, if the rarer allele has a frequency of at least 0.01, so that the heterozygote frequency is at least 0.02, the locus is considered to be polymorphic.

"Restriction Fragment Length Polymorphism (RFLP)." A RFLP is a polymorphism in the DNA sequence that can be detected on the basis of differences in the length of DNA fragments produced by digestion with a specific restriction enzyme.

"Penetrance." The frequency of expression of a genotype is its penetrance. When the frequency of expression is less than 100%, the trait is said to exhibit reduced penetrance or lack of penetrance. In an individual who has a genotype that characteristically produces an abnormal phenotype but is phenotypically normal, the trait is said to be nonpenetrant.

DETAILED DESCRIPTION OF THE INVENTION

The invention is based on the results of linkage analyses with the locus responsible for early-onset idiopathic torsion dystonia, DYT1, on chromosome 9q. This analysis has demonstrated that this locus is the torsion dystonia gene in a large fanlily whose members are genetically susceptible to the development of torsion dystonia. This locus is further implicated in the susceptibility to the development of torsion dystonia in the Jewish population.

From this data, it was inferred that the torsion dystonia locus for this form of dystonia resides on human chromosome 9q and specifically between 9q32-q34.

These studies have resulted, for the first time, in a general method for detecting the presence of at least one form of torsion dystonia which comprises analyzing the human chromosome 9q for a DNA polymorphism linked to torsion dystonia.

Any of a variety of restriction fragment length polymorphisms (RFLP's) can be used.

In particular, this test is carried out by studying the heritability, in a combination of family members which allows the de. termination of phenotype, of one DNA polymorphism or a combination of two or more polymorphisms linked to torsion dyatonia. The test can be used prenatally to screen a fetus or presymptomatically, to screen a subject at risk through his/her family history. The method can also be used to screen for a particular haplotype in an individual. The presence of the haplotype is correlated with the susceptibility or development of torsion dystonia.

The haplotype associated with torsion dystonia, particularly in the Jewish population, has been designated "4A12" haplotype. This haplotype is presently characterized by the following markers:

| (Markers Used) | 1AG5 | 1AB9 | 2BH10 | ABL | ASS | 1AC6 |
|---|---|---|---|---|---|---|
| (Alleles in disequilibrium) | 2 | 16 | 8 | 4 | A12 | 2/10 | the 4A12 haplotype for markers ABL/ASS are as follows:

The ABL/4 allele is identified by a 141 base pair (bp) fragment found using the primers described in Kwiatkowski et al. *Am. J. Human Genet.* 48:121–128 (1991) and Kwiatkowski, D. *Nuc. Acids Res.* 19:4967 (1991); both references herein incorporated by reference.

The ASS/A12 allele is identified by a 106 bp fragment using the ASS-A and ASS-C primers described in Kwiatkowski et al. (1991) supra.

Other probes may also be useful, for example, using the ASS G1 probe a 9.9 kb band is detected; using ASSG3 a 6.0 kb band is detected. These two bands, 9.9 kb and 6.0 kb identify the A haplotype described in Northrup et al., *Genomics* 5:442–444 (1989), herein incorporated by reference. See also: Lander et al., *Genomics* 1:174–181 (1987); Lathrop et al., *Genomics* 3:361–336 (1988); and Lee et al., *Adv. Neurol.* 14:137–151 (1988).

Now that the location of the dystonia gene has been identified other markers can be found using methods known in the art. Generally, primers are utilized which will identify markers associated with dystonia, for example (GT)n and RFLP markers.

To identify useful primers, the following procedure may be followed. Gertomit clones are made from the chromosomal region of the dystonia gene. The genomic clones which map back to the dystonia region are digested with a restriction endonuclease; subjected to gel electrophoresis; and, hybridized to a GT oligonucleotide. Those bands which hybridize with the GT oligonucleotide are subcloned and sequenced. Primers are made which correspond to the unique sequences flanking GT repeat regions. (GT)n polymorphisms are discussed in Weber, J. L. *Genomics* 7:524–530 (1990).

The primers are used in a polymerase chain reaction with DNA from an individual to determine the presence or absence of a particular marker.

The invention also extends to products useful for carrying out the assay, such as DNA probes (labelled or unlabelled), kits, and the like.

At its broadest, the invention comprises detecting: the presence of the gene for torsion dystonia by analyzing human chromosome, particularly 9q or 11q, for DNA polymorphisms linked to torsion dystonia (Ozelius, L., et al., *Neuron* May 19, 1989, incorporated herein by reference).

The genetic linkage or connection between the desired polymorphisms and the torsion dystonia gene was determined by analyzing a combination of familial relatives of the subjects under investigation. The combination was chosen so that it would allow determination of the torsion dystonia phenotype linked to the presence of the polymorphism. Thus, several individuals were examined. For the most part, these included an unaffected parent, an affected parent, an affected sibling, an unaffected sibling, as well as other, perhaps more distant members. Ideally, an unaffected parent, an affected parent and an affected sibling should be utilized. If an affected parent is deceased, satisfactory results can still be obtained if unambiguous segregation of the polymorphism with the torsion dystonia gene can be demonstrated in other members.

The use of RFLP's is only one preferred embodiment of detecting the polymorphism. The most common methodology for detecting the presence of a RFLP at present is to carry out restriction analysis using a given enzyme, perform a Southern hybridization procedure with the desired probe and identify a given RFLP or RFLP's. The use of RFLP's in linkage analysis and genetic testing is well known in the art (for example see Gusella, U.S. Pat. No. 4,666,828, incorporated herein by reference, and Donis-Keller, H. et al., *Cell* 51:319–337 (1987)).

For analysis using RFLP's, it is necessary to obtain a sample of the genetic material from all individuals being studied, including the subject. Preferably, a blood sample is used as the source of geodetic material and the lymphocyte DNA analyzed. Ill desired, the DNA may be extracted from the lymphocytes prior to genetic testing. For detection of RFLP's, the DNA in the sample is digested with a given restriction endonuclease. Alternatively, several digests can also be obtained. If necessary, the DNA may be amplified prior to RFLP analysis. After the digest is obtained, and the same is separated by a standard technique such as, for example, agarose gel electrophoresis, the separated bands are probed with a DNA fragment coding for the RFLP sequence. There may be an optimum combination of restriction enzyme and probe. For example, in the hereinafter described MID GSN probe, restriction enzymes such as StuI can be utilized. The M1D GSN probe was previously called GM1 and its construction and sequence have been published (Kwiatkowski, D. J. et al., *Nature* 323:455–458 (1986), incorporated herein by reference the nucleotide and predicted amino-acid sequence of human plasma gelsolin cDNA described in FIG. 1 of Kwiatkowski is set forth herein as SEQ ID NO: 1 and 2, respectively; GM1 was isolated by screening a cDNA library using a $^{32}$P-labelled single-stranded M13 probe derived from the 201 bp EcoRI-BglII 5' fragment (bases 23–224) subcloned into M13mp19). Preferably, more than one polymorphism (i.e., more than one probe) is utilized for the detection. Ideally, a different polymorphism on either side of the torsion dystonia gene is detected so as to increase the sensitivity significantly. As described hereinbelow, additional probes that can be used include, for example, D9S10 and ASS. It is not necessary that the probe be a DNA probe. For example, RNA probes can be used.

Since, ultimately, the use of RFLP's depends on polymorphisms in DNA restriction sites along the nucleic acid molecule, any method capable of detecting the polymorphisms can also be used. Techniques such as amplification of a desired region of the chromosome coupled with direct sequencing, or location of polymorphisms on the chromosome by radiolabelling, fluorescent labelling or enzyme labelling can also be utilized. M described below, (GT)n polymorphisms are highly informative in identifying markers associated with dystonia.

If the genetic sample to be analyzed is present int limited amounts, the nucleic acid within such sample may be first amplified so as to increase the signal for subsequent analysis such as RFLP or sequencing analysis. DNA may be amplified using any DNA amplification technique, for example, the polymerase chain reaction (Mullis, K. et al. *Cold Spring Harbor Symp. Quant. Biol.* 51:263-273 (1986), Erlich, H. et al., EP 50,424; EP 258,017, EP 237,362; Mullis, K., EP 201,184; Mullis, K. et al., U.S. Pat. No. 4,683,202; and, Loh et al., *Science* 243:217-222)). Li et al., *Nature* 335:414-417 (1988), has reported the use of the polymerase chain reaction to coamplify two genetic loci from a single sperm to levels capable of genetic analysis. An advantage of the technique of Li et al. is that a large number of meiotic products can be examined from a single individual allowing determination of the recombination frequency between genetic markers which are physically very close.

DNA and/or RNA may also be amplified using an amplifiable RNA sequence as a probe and Qβ-replicase (Chu, B. C. F. et al., *Nucl. Acids Res.* 14:5591-5603 (1986)).

The polynucleotide probes may be RNA or DNA and preferably DNA, and can be labelled by standard labelling techniques such as with a radiolabel, enzyme label, fluorescent label, biotin-avidin label, and the like, which allow for their detection after hybridization (for example, see Leary, J. J. et al., *Proc. Natl. Acad. Sci., USA* 80:4045 (1983)).

Comparison of the RFLP or RFLP's for affected and unaffected individuals in the family line of the subject, with the RFLP or RFLP's for the subject under investigation will quickly reveal the presence or absence of the torsion dystonia gene in the subject. The results are best expressed in terms of probability of presence of the torsion dystonia gene in the subject.

Although the work described hereinafter is specifically addressed to the MID GSN probe (Kwiatkowski, D. J. et al., *Am. J. Hum. Genet.* 42:565-572 (1988)), other genetic sequences useful for probes can readily be obtained. For example, methods for generating additional new DNA fragments also linked with the torsion dystonia gene are as follows.

A first method is to test randomly chosen pieces of human (either genomic or cDNA clones) DNA fragments that map to the appropriate region of chromosome 9. Such mapping can be achieved by three techniques:

(a) hybridization to DNA from a panel of somatic cell hybrids;

(b) in situ hybridization to metaphase chromosome spreads; or (c) genetic linkage to GSN, D9S10, D9S26, ABO or any other marker as already mapped to the region.

For methods (a) and (b), the new fragment need not be polymorphic, but for (c), polymorphisms must first be identified by comparing the restriction pattern of the genomic DNA at the new site in unrelated individuals. In methods (a) or (b), the mapped fragment must still be shown to detect a polymorphism in human DNA. The polymorphism which represent a new genetic marker can then be tested for linkage for torsion dystonia in family studies as in this application.

A second, more efficient, method to generate additional DNA probes is to make a recombinant DNA library somatic cell hybrid line in which chromosome 9, or especially 9q or a piece of it is either one of a few or the only human chromosome present in a cell where all other chromosomes are form another species (usually mouse, hamster or rat). Recombinant clones containing human DNA are then identified by hybridization to species-specific repetitive sequences. If the hybrid cell contains only chromosome 9, or a portion of it, clones containing human DNA must contain DNA from chromosome 9. If other human material is present in the hybrid, then one must additionally resort to one of the mapping methods outlined in the previous paragraph.

A third method for obtaining DNA clones from chromosome 9 is to construct a library from human DNA isolated from metaphase chromosomes that have been sorted on a fluorescence activated sorter (*Human Genetic Diseases, A Practical Approach*, K. E. Davies, IRL Press, Washington, D.C., 1986). This method can sometimes yield purified chromosomes of 95% or greater purity. This method can also be used in combination with the method described above for generating a recombinant DNA library somatic cell hybrid line.

A final method of obtaining new DNA probes from the torsion dystonia region is to use any probes already mapped to the region in order to "fish out" adjacent overlapping pieces of DNA from gertomit libraries (commonly called "chromosome walking"). In this case, the primary probe mapped to chromosome 9 need not be polymorphic.

In all the cases outlined above, a probe must ultimately be found to detect a polymorphism if it is to be useful for testing torsion dystonia. The polymorphism must be found to be linked to torsion dystonia or to other useful markers in family studies, or to be immediately adjacent to preexisting markers.

The particular polymorphism probe can be of any desired sequence length as long as it is capable of identifying the polymorphism in the involved DNA region or locus. It can be a DNA or RNA fragment by itself, or be present in longer genetic sequences or fragments, or even in a plasmid or other appropriate vehicle. Labelling and hybridization conditions can be readily determined by those of skill in the art as described above. Usually, the stringency is standard for unique sequence DNA from within the species. A detailed discussion of nucleic add hybridization technology may be found in *Nucleic Acid Hybridization*, B. D. Hames et al., eds., IRL Press, Washington, D.C., 1985.

Probes for the detection of torsion dystonia may be DNA or RNA as described above and may be synthesized chemically or enzymatically, for example, as described in *Oligonucleotide Synthesis, A Practical Approach*, M. J. Gait, ed., IRL Press, Washington, D.C., 1984. Probes may also be obtained and replicated by insertion into a plasmid using techniques known to those of skill in the art ((Maniatis, T. et al., *Molecular Cloning (A Laboratory Manual)*, Cold Spring Harbor Laboratory, 1982).

If the polymorphism is found in a gene product, such as a mRNA, the presence of that polymorphic mRNA may be assayed for directly with the probe and especially with an antisense RNA probe.

The test can be carried out prenatally or, in young or adult individuals, presymptomatically.

Utilizing the methods set forth above, the involvement of the dystonia gene on 9q in two forms of hereditary dystonia with early onset has been confirmed. Furthermore, now that the chromosomal location of this gene (DYT1) has been defined to a small region, the region can be cloned and characterized by general methods known in the art.

At least two other autosomal genes can produce dystonia. One of these appears to map to a region of 11q believed to be related to the critical region on 9q. The region of 11q can be characterized by similar methods described herein. Initial studies indicate that the 11q22–q23 region contains the gene in an American family with myoclonie dystonia.

As set forth in the Experimental section, a dystonia gene has been localized to a 6 cM region on chromosome 9q34 between loci AK1 and ASS in Jewish families. A strong association of one haplotype for ASS with the dystonia gene in this population was observed.

The method lends itself readily to the formulation of kits which can be utilized in diagnosis. Such a kit would comprise a carrier being compartmentalized to receive in close confinement one or more containers wherein a first container may contain DNA containing coding sequences for a given polymorphism, e.g., a RFLP. A second container may contain a different set of sequences coding for a second RFLP., and so on. The kit may also contain oligonucleotide primers for unique markers. Other containers may contain reagents useful in the localization of the labelled probes, such as enzyme substrates. Still other containers may contain restriction enzymes, buffers, and the like.

Having now generally described the invention, the same will be understood by reference to certain specific examples that are provided herein for purposes of explanation only and are not intended to be limiting unless otherwise specified.

EXAMPLES

Example 1

Neurological Evaluation of a Family Inflicted with Dystonia

The family under study consists of 165 members. For this linkage study blood samples have been analyzed and neurologic examinations carried out on 73 and 74 members, respectively (FIG. 1).

The clinical expression of dystonia can be varied and the examiners specifically sought to elicit dystonia and distinguish it from other movement disorders (Fahn, S., Neurol. Clin. 2:541–554 (1984)). The purpose and nature of the study were explained to all family members. All cooperative members of this family gave informed consent and then were given complete on-site neurologic examinations by neurologists experienced in evaluating dystonia and blood samples were drawn. All but three individuals were videotaped, and recordings were analyzed by a panel of four neurologists at the Dystonia Clinical Research Center. The videotape examination showed the subject sitting at rest, hands in lap and outstretched; standing; and walking. Speech was analyzed by listening to the patient talk. The arms were evaluated by having the subject perform the finger-to-nose maneuver, write with each hand, and carry out rapid repetitive movements of the fingers and hands. The legs and feet were evaluated by having the subject carry out analogous rapid repetitive movements and by observing legs and feet when the subject was walking.

Each subject was classified as having definite dystonia, probable dystonia, possible dystonia, no dystonia or unrated. The designation of definite dystonia was made when unequivocal features of dystonia were observed, such as twisted movements or postures, not due to other possible underlying neurological conditions. The designation of probable dystonia was made when there were findings highly suggestive of dystonia; examples include awareness of abnormal movements by the subject, occasional twisting of a hand or foot, and tightness without twisting of arm muscles with handwriting or of leg muscles with foot maneuvers. The designation possible dystonia was applied when the examination was abnormal but not diagnostic of dystonia; it was applied, for example, when there was clumsiness with foot-tapping or too tight a grip on the pen when writing. The term unrated was applied when the subject had another condition that could obscure the presence of dystonia or be a cause of dystonia. Examples were the presence of a neurological condition (e.g., Parkinson disease, stroke, poliomyelitis, head trauma, encephalitis), an orthopedic condition (e.g., frozen shoulder, severe rheumatoid arthritis), or a history of prenatal or perinatal injury.

No subject was given a rating of definite dystonia without verification by videotape review. None of the five family members examined in person, but without a videotape exam, were rated as definite dystonia. Of these five subjects, one was rated a probable dystonia by two examiners independently on separate examinations (and left as probable dystonia in the final analysis), one as unrated because of the presence of strokes and rheumatoid arthritis, and three as not having dystonia by the examiner. Similarly, family members considered by Johnson et al. (Johnson, W. et al., Arch. Neurol. 7::301–313 (1962)) to have dystonia, who were no longer alive, were listed as probable dystonia.

Age of onset was determined as the first occurrence of dystonic movements as noticed by the patient or his/her relatives in this or the preceding study (Johnson, W. et al., Arch. Neurol. 7:301–313 (1962)). The history was confirmed by personal interviews by the current team of clinical investigators.

The pedigree of this family is shown in FIG. 1. Only individuals who fulfilled rigorous criteria for dystonia (Fahn, S., Neurol. Clin. 2:541–554 (1984)) on videotape review have been considered affected for purposes of this linkage analysis. This includes 14 individuals with dystonic manifestations affecting cranial structures, limbs and trunk, with onset between 4 and 43 years, average age 14.4±3.1 and median 10.0. The apparent penetrance is 75%, considering only individuals with definite dystonia who are over the mean age-of-onset. Three individuals, who had some dystonic features (1 probable and 2 possible affected) each produced an affected offspring.

Example 2

Linkage Analysis with the DTY1 Dystonia Locus

DNA Probes and Labeling

DNA probes were labeled routinely with [$^{32}$P]dATP (3000 Ci/mmol; Amerhsam) by random oligonudeotide priming (Feinberg, A. P. et al., Anal. Biochem. 137:266–267 (1984)). Gel-purified insert fragments were used for probes M1D, ASSG2, ASSG3 and pEDZ19.3. In some cases human placenta DNA was hybridized to labeled probes prior to hybridization with gertomit DNA to saturate repeat sequences.

The following polymorphic marker probes on 9q were used: ASSG2 and ASSG3 (SphI and PstI) for the argininosuccinate synthetase locus (ASS) (which maps to q34-qter; Beaudet, A. L. et al., Cell 30:287–293 (1982); Northrap et al., manuscript in preparation)); pMCT136 (PstI) and pEKZ19.3 (TaqI) for random VNTR loci D9S10 and D9S17, respectively (q34 by linkage mapping; Kumlin-Wolff, E. et al., Nucleic Acids Res. 15:10610 (1987); Carlson, M. et al., Nucl. Acids Res. 15:10613 (1987); Lathtop, M. et al., Genomics 3:361–366 (1988)); CRI-L659 (TaqI) for random locus D9S26 (q31–34) by linkage mapping (Donis-Keller, H. et al., Cell 51:319-337 (1987)); M1D (StuI) for the gelsolin locus (GSN) (q32-34; Kwiatkowski, D. J. et al., Am. J. Hum. Genet. 42:565-572 (1988); Kwiatkowski et al., Nucleic Acids Research, (1989). References to map positions for all loci, and RFLPs for all loci except ASS and GSN are cited in Human Gene Mapping (HGM): volumes 9 (1988) and 9.5 (1989), S. Karger AG, Basle, Switzerland (published as part of Cytogenetic and Cell Genetics).

RFLP Analysis

DNA was extracted from lymphoblast lines (Anderson, M. A. et al., In Vitro 29:856-858 (1984)) or whole blood, as described (Gusella, J. et al., Natl. Acad. Sci. USA 6:5239-5243 (1979); Breakefield, X. O. et al., J. Neurogenet. 3:159-175 (1986)). Five 10 μg samples of DNA were digested to completion with restriction enzymes according to manufacturer's instructions. Electrophoresis was carried out routinely in 0.8% agarose gels at 70-90 V for 16 hr. DNA fragments were blotted onto Genetran (Plasco) by the method of Southern (Southern, E., Meth. Enzymol. 68:152-176 (1979)). Filters were prehybridized and hybridized in 0.3% SDS, 1× Denhart's, 6× SSC containing salmon sperm DNA at 65° C.; washed at 65° C. in decreasing concentrations of SSC to 0.5 x and exposed to X-ray film, as described (Breakefield, X. O. et at, J. Neurogenet. 3:159-175 (1986)).

Two-point Linkage Analysis

To date over 240 polymorphic marker probes and 15 blood group and protein markers representing all 22 autosomes have been evaluated in this family (Breakefield, X. O. et al., J. Neurogenet. 3:159-175 (1986); Kramer, P. L. et at, Adv. Neurol. 50:57-66 (1988)). About 60% of the human genome has been excluded as containing the dystonia gene on the basis of two-point linkage analysis, assuming a human haploid genome size of 3300 cM. Exclusion of the disease gene from close proximity to these markers was established by a lod score ($\log_{10}$ odds ratio) of −2 or less. This dystonia gene will be referred to here as DYT1 for the first locus found which is responsible for idiopathic torsion dystonia.

Two-point linkage analysis for the dystonia-to-marker comparisons was performed using the FORTRAN computer program LIPED version 3 (Hodge, S. E. et at, Am. J. Hum. Genet. 31:761-762 (1979); Ott, J., Am. J. Hum. Genet. 28:528-529 (1976)) which incorporates an age-of-onset correction. Autosomal dominant inheritance of a rare gene (frequency 0.01%) was assumed for dystonia. An estimate of 0.75 for the maximum penetrance was obtained using the "singles" method (Davie, A. M., Annals Hum. Genet. 42:507-512 (1979)). Only those individuals considered unanimously and unequivocally to have dystonia were designated as definitely affected. Those individuals whose clinical designation was "possible" or "probable" dystonia were considered "unknown" in this linkage analysis. All others were considered unaffected.

Parameters for the age correction in the two-point analysis were based on empirical age-of-onset data from this family (Breakefield, X. O. et al., J. Neurogenet. 3:159-175 (1986)). Specifically, penetrance between the ages of 5 and 35 increased in a straight-line fashion from 0.0 to 0.75, respectively. Penetrance prior to age five was set at 0.0 and that after age 35 was held constant at 0.75.

Several areas of the genome in which markers gave lod score ≧0.6 were highlighted for further study, including the ABO locus on 9q. A number of DNA marker probes on 9q were evaluated by two-point analysis with the DYT1 locus, including those shown in Table 1. Highest lod scores were obtained with a cDNA probe for the gelsolin (GSN) locus, which maps centromerie to ABL on 9q32-q34 using somatic cell hybrids containing translocations of this human chromosome (Kwiatkowski, D. J. et al., Am. J. Hum. Genet. 42:565-572 (1988)). The DYT1 and GSN loci showed significant evidence for linkage with a maximum likelihood estimate of theta, $\theta$, at 0.0 of Z=3.51. The 1-lod-unit interval for this estimate is approximately 0 to 18 cM. In fact, no obligate recombinations between GSN and DYT1 were observed in 67 meioses, although most were not fully informative.

Results of two-point linkage: analyses with this dystonia locus and other 9q markers in this region, which were informative, are given in Table 1. They include D9S26, ABO, ASS and D9S10, all of which gave positive lod scores. (Markers at the ABL locus were uninformative in this family). Negative evidence for linkage was obtained with D9S17, which lies 12 cM distal to D9S10. In order to assess the effect of varying the estimate of penetrance on the linkage results, the six 9q markers reported in Table 1, were analyzed using penetrance estimates of 0.50 and 0.90. With respect to the two-point analyses, no marked differences in the lod scores were evident, relative to those obtained with penetrance=0.75. The largest differences occurred with the GSN locus. Specifically, lod scores obtained using penetrance=0.90 increased by about 0.20, across all $\theta$ values. Nonetheless, even with the lowest penetrance estimate, significant evidence for linkage of GSN and DYT1 was obtained ($Z_{max}$=3.10 at $\theta_{max}$=0.0).

TABLE 1

Results of Pairwise Linkage Analysis of DYT1 (Idiopathic Torsion Dystonia 1) and Markers on Chromosome 9q

| Symbol | .001 | .05 | .10 | .20 | .30 | .40 | $\theta$ | Z |
|---|---|---|---|---|---|---|---|---|
| D9S26 | −0.69 | +0.88 | +1.05 | +0.99 | +0.71 | +0.31 | 0.13 | 1.06 |
| GSN | +3.50 | +3.26 | +2.99 | +2.36 | +1.61 | +0.74 | 0.00 | 3.51 |
| ASS | +0.17 | +0.35 | +0.41 | +0.37 | +0.23 | +0.07 | 0.12 | 0.41 |
| ABO[b] | −0.44 | +1.08 | +1.19 | +1.03 | +0.66 | +0.23 | 0.10 | 1.19 |
| D9S10 | +0.73 | +2.18 | +2.20 | +1.85 | +1.26 | +0.52 | 0.08 | 2.22 |
| D9S17 | −6.64 | −3.60 | −2.12 | −0.80 | −0.26 | −0.06 | 0.50 | 0.00 |

[a]Linkage analysis was carried out assuming a penetrance of 0.75 for the DYT1 gene.
[b]This data was obtained for only a portion of the pedigree (Falk, C.T. et al., Adv. Neurol. 50:67-72 (1988)) and were reanalyzed with updated status on affected members.

Multi-point Analysis

Multi-point analysis was performed using the LINKMAP program from the computer package LINKAGE version 4.7 assuming no interference (Lathrop, G. M. et al., Am. J. Hum. Genet. 42:498-505 (1988)). The stepwise age correction incorporated into this analysis is technically more precise than the correction used in the two-point analysis; however, in practice differences are negligible. In this family, about 50% of affected individuals had onset by early adolescence (12-14 years), and about 75% had onset by mid-20s. To account for this distribution, six liability classes were defined in which penetrance increased from 0.0 at age 5 to 0.75 at age 35, after which penetrance remained constant at 0.75. No interference was assumed.

Multi-point analysis was carried out using the dystonia locus and three informative loci on 9q, D9S26, ABO and D9S10. These three loci were chosen for the 4-point analysis for several reasons: (1) the results of two-point analyses with these loci and DYT1 gave suggestive, though not statistically significant, evidence for linkage; (2) these markers span an interval which encompasses the region in which the GSN locus apparently lies (Kwiatkowski, D. J. et al., *Am. J. Hum. Genet.* 42:565-572 (1988)); and (3) reliable estimates of distance between these loci are available from the Centre d'Etude de Polymorphism Humain (CEPH) reference pedigrees except that a 9q linkage map including the GSN and ASS loci was not yet available. The genetic map distances for ABO, D9S26 and D9S10 were obtained from 40 pedigrees constituting the CEPH. The distance between D9810 and ABO has been taken from Lathrop, G. M. et at, *Am. J. Hum. Genet..* 42:498-505 (1988), as this data was not available from the CEPH Database. The maximum likelihood order and $\theta$ estimates were determined using the MAPMAKER program (Version 1.0; Lander, E. S. et at, *Genomics* 1:174-1.81 (1987)).

Figure 2:
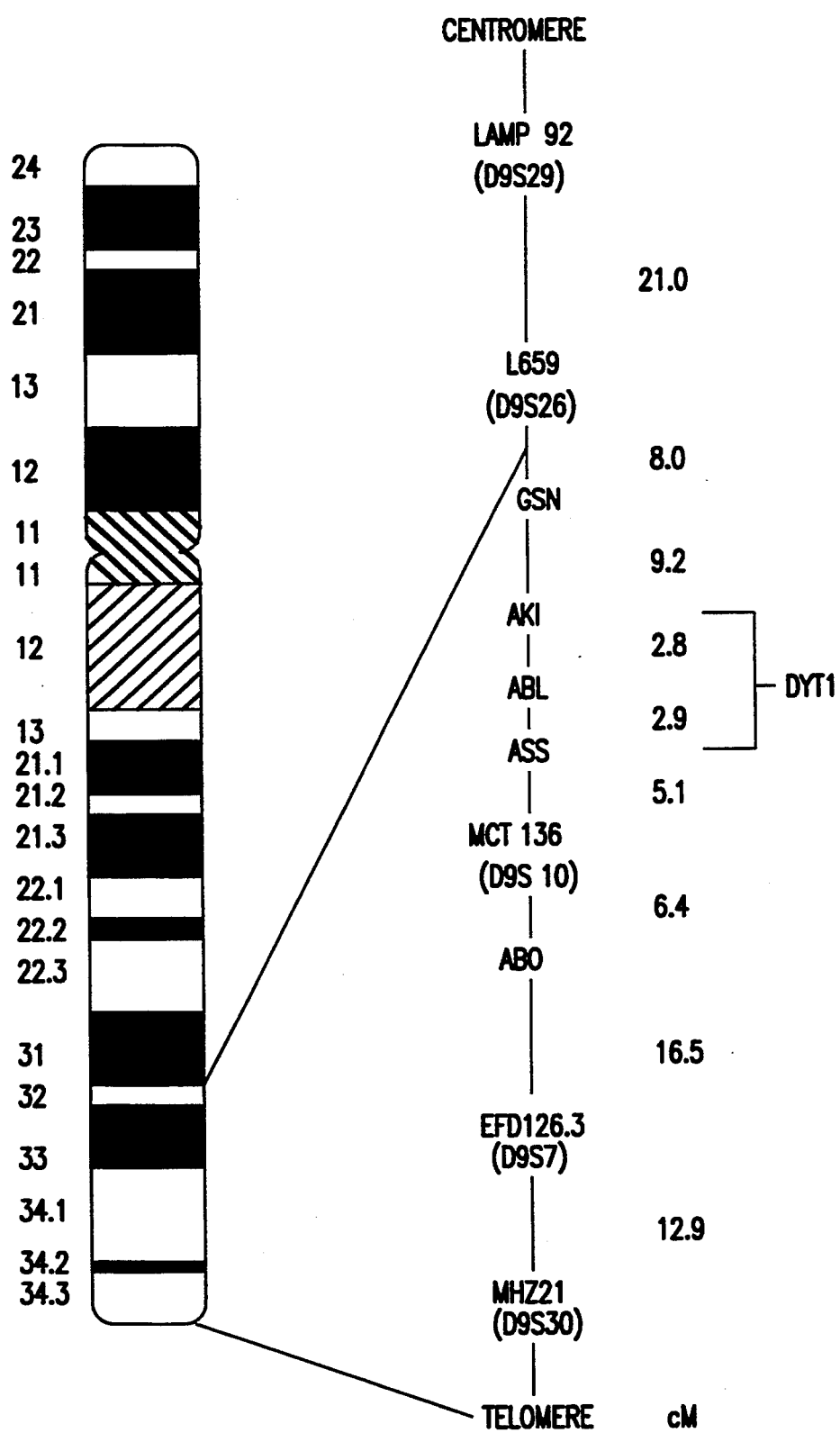
FIG. 2 is a human 9 chromosome map showing physical assignments and linkage distances in q32-34 region. Map distances are given as recombination fractions of sex average values; scale is in genetic distance (Morgans). Modified from Lathrop, M. et al., *Genomics* 3:361-366 (1988).
Figure 3:
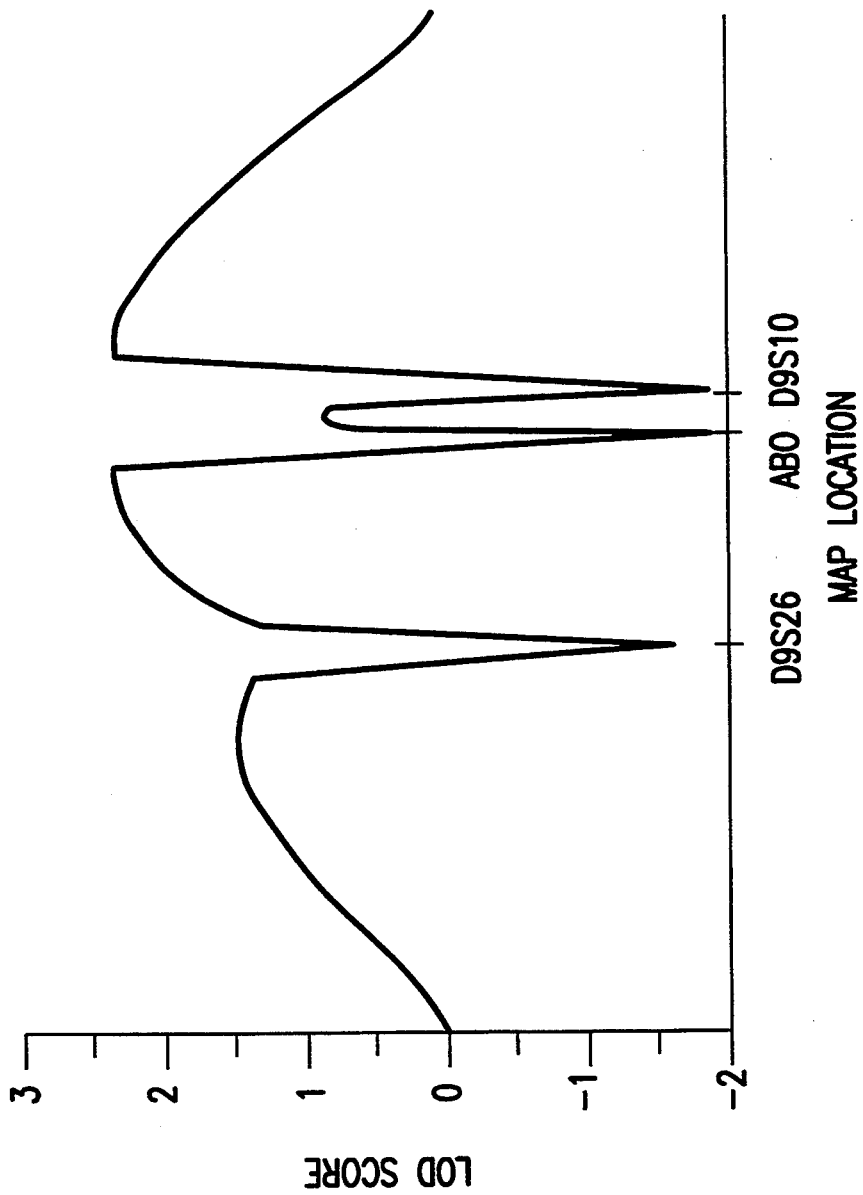
FIG. 3 shows the results of multipoint analysis. of ITD1 (DYT1) and 9q markers. Location map summarizing lod scores calculated for dystonia at various map positions in a fixed marker map. Genetic distances for markers are the same as in FIG. 2.

Results of the multi-point analysis are presented graphically in FIG. 3. On the basis of the preliminary linkage map given in FIG. 2, the DYT1 locus appears to be centromeric to ABO. Although statistically significant lod scores were not obtained, the most likely position of the disease locus is about 9.5 cM from ABO (Z=2.46). Thus, the multi-point linkage results are consistent with the two-point results which suggest close linkage between GSN and the DYT1 loci.

Although the GSN locus is known to be on 9q near the ABL locus, its precise map location in this region has not yet been established using CEPH reference pedigrees. We obtained an approximate map location of GSN, relative to D9S26, ABO and MCT136, based on data available in the family studied here. On the basis of this sample, the most likely position of GSN is approximately 7 cM distal to D9S26 (although the odds of GSN being anywhere within the region spanned by D9S26-ABO were greater than $10^8:1$). We then performed a 5-point linkage analysis of DYT1 with D9S26, GSN, ABO and MCT136, using this tentative location for GSN. The most likely position of DYT1 is at the GSN locus itseft (Z=3.57 at $\theta$=0.0); however, significant lod scores (>3.0) were obtained within the interval 3.5 cM proximal to GSN and 15 cM distal to GSN. Thus no matter where the GSN locus falls within this 18 cM region, the multipoint results strongly support the location of the DYT1 gene in this region between D9S26 and ABO.

This linkage study places a gene causing susceptibility to idiopathic torsion dystonia (DYT1) in a non-Jewish family to within 18 cM of the gene encoding gelsolin ($\theta$=0.0, Z=3.51, 1-lod-unit interval 0-18 cM). This lod score corresponds to odds of greater than $10^3:1$ in favor of linkage of these two loci. Multipoint analysis suggests that both GSN and DYT1 lie between D9S26 and ABO. Generation and evaluation of additional 9q probes in this region will allow definition of closely flanking markers around the dystonia locus in this family.

Two genes in the 9q region could be considered as candidate loci for the DYT1 gene based on current knowledge of genes that map in this region and features of dystonia. It seems possible that a protein that influences developmental organization, even non-specifically, might produce subtle alterations in neuronal circuitry underlying dystonic symptoms. In this category, gelsolin (GSN) is a $Ca^{2+}$ and polyphosphoinositide-regulated, multifunctional, actin-binding protein which is widely expressed in mammalian tissues, including brain (Kwiatkowski, D. J. et al., *J. Biol. Chem.* 263:8239-8243 (1988)). It is thought to regulate actin filament architecture during cell movement (Matsudaira, P. et al., *Cell* 54:139-140 (1988); Yin, H. L., BioEssays 7:176-179 (1988)) and is likely to participate in the motile activity of neuronal growth cones (Forscher, P. et al., *J. Cell. Biol.* 107:1505-1516 (1988)). Another candidate is a protein involved in maintaining the balance between catecholaminergic and cholinergic inputs to the basal ganglia; the gene for dopamine-beta-hydroxylase (DBH), an enzyme that converts dopamine to norepinephrine, also maps to the 9q34 region (Lamouroux, A. et al., *EMBO J.* 6:3931-3937 (1987); Craig, S. P. et al., *Cell Genet.* 48:48-50 (1988); Wilson, A. F. et al., *Am. J. Hum. Genet.* 42:160-166 (1988)).

Several lines of evidence argue against a deficiency of DBH being involved in dystonia. Individuals who appear to be deficient in serum DBH suffer from severe orthostatic hypotension and do not show dystonic symptoms (Veld, A. J. M. et al., *Lancet* 183-187 (1987); Robertson, D. et al., *N. Engl. J. Med.* 314:1494-1497 (1986)). Normal or elevated levels of DBH have been reported in serum of dystonic patients, including members of this family (Ziegler, M. G. et al., *Adv. Neurol.* 14:307-315 (1976); Wooten, G. F. et al., *N. Engl. J. Med.* 288:284-287 (1973)). Further, the dominant mode of inheritance in this disease would argue against its being caused by a loss of enzyme activity.

Rather than a deficiency of DBH, it is more likely that abnormally high expression of DBH due to a mutation in or near the DBH locus is involved. In three cases of idiopathic, non-Jewish dystonia increased levels of norepinephrine were observed in several regions of the upper and lower brainstem (Hornykiewizc, O. et al., *In Advances in Neurology (Dystonia* 2) 50: S. Fahn, C. D. Marsden, and D. B. Calne, eds. (New York: Raven Press), pp. 157-165 (1988); Jankovic, J. et al., *N. Eng. J. Med.* 316:278-279 (1987)). In addition, genetically dystonic rats and mice show elevated norepinephrine in the locus coeruleus, and neurophysiologic studies in experimental animals implicate hyperactivity of norepinephrine neurons in this brain area in dystonic symptoms (Lorden, J. F. et al., *Adv. Neurol.* 50:277-297 (1988); Duehen, L. W., *Adv. Neurol.* 14:353-365 (1976); Adams, L. M. et al., *Adv. Neurol.* 50:313-333 (1988)). Consequently, treatment of dystonia is possible by administering to patients efficacious levels of anti-norepinephrin,e drugs or other adrenergic blocking agents, for example, $\beta$-blockers, monoamine oxidase inhibitors, acetylcholinesterase inhibitors, and neuroleptic agents, and especially phenothiazines, butyrophenones, phenoxybenzamine, phentolamine, tolazoline, prazosin, clonidine, $\alpha$-methyldopa, guanethadine, and reserpine.

Example 3

Cell lines

Over the past year we have established lymphoblast lines and prepared DNA from 251 new individuals (Table 2). Together with samples banked in previous years this now includes 841 individuals representing 86 families with nine different forms of hereditary dystonia, as well as two families with balanced translocations involving the 9q34 region. Most of these samples have been provided by Dr. Fahn's group, but thirteen other physicians have also sent samples. We have also obtained information from Dr. Amos Korcyzn in Israel about 7 families with multiple affected members and sent him supplies for collecting and mailing samples. Eight blood samples from affected individuals from different families representing hereditary dystonia with other neurologic symptoms of mental retardation and/or dysmorphology were sent to Dr. Bruce Korf's laboratory (Children's Hospital) for high resolution cytogenetic analysis; no chromosomal abnormalities were observed.

Location of the 9q34 Dystonia Gene
a) Flanking markers

We have now collected and generated over 30 polymorphic DNA probes in the 9q32-34 region. We are in the process of positioning these markers within a linkage map of the area, which was described originally by Lathrop et al. (1988). So far we have carried out linkage analysis on 10 of these marker probes in both Venezuelan and Centre D'Etude Polymorphisme Humain (CEPH) reference pedigrees consisting of over 800 people. We have placed two new marker loci on the map, GSN (gelsolin) and Lamp92, and repositioned two others, MCT136 and L659. The dopamine beta-hydroxylase (DBH) gene has not been placed definitively, but appears to lie very close to ABO. Computerized analysis of this data using MAPMAKER has provided a working map, which has been used for multipoint analysis in dystonia families.

Figure 4:
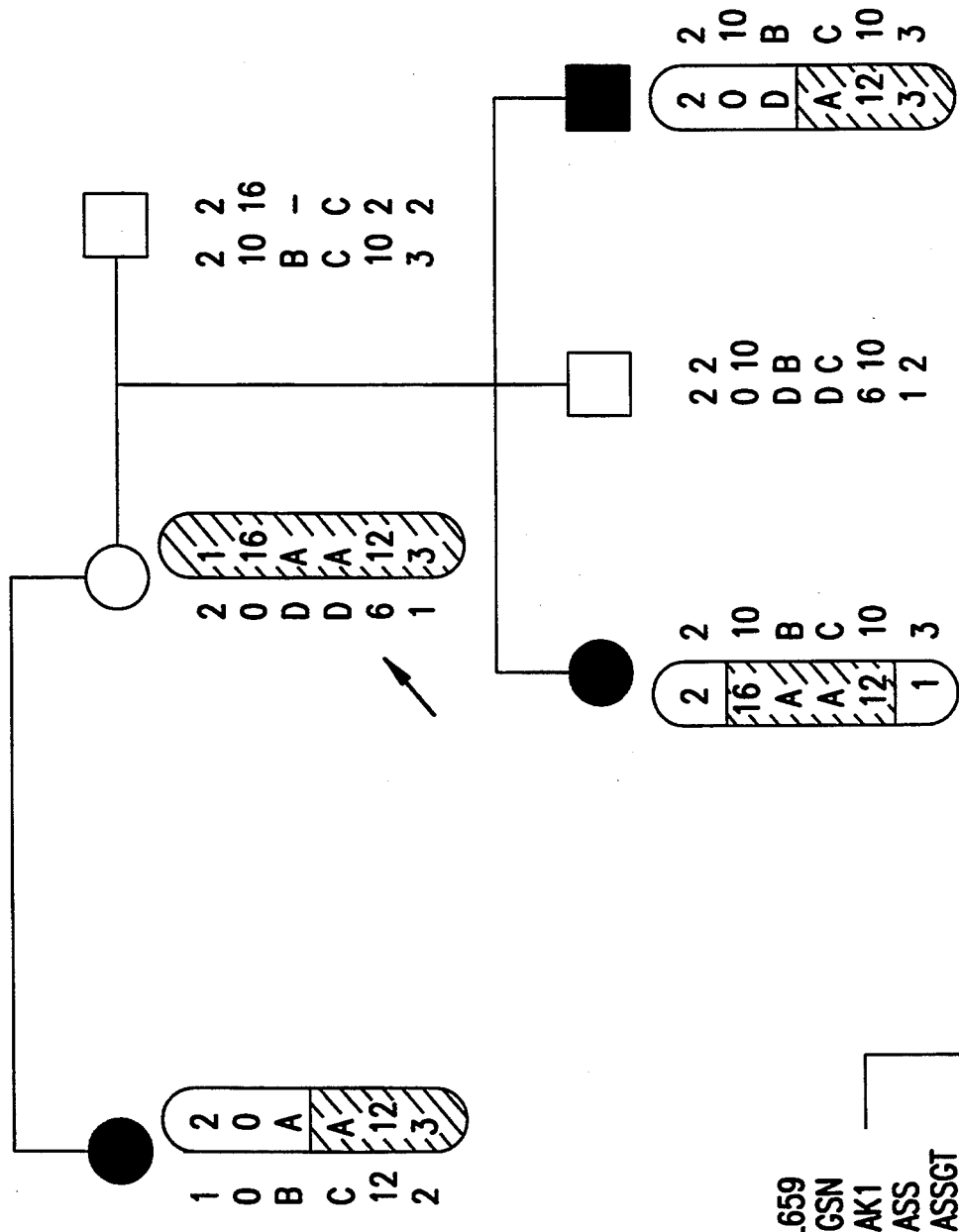
FIG. 4 shows the segregation of dystonia gene and marker alleles in a Jewish family.
Figure 5:
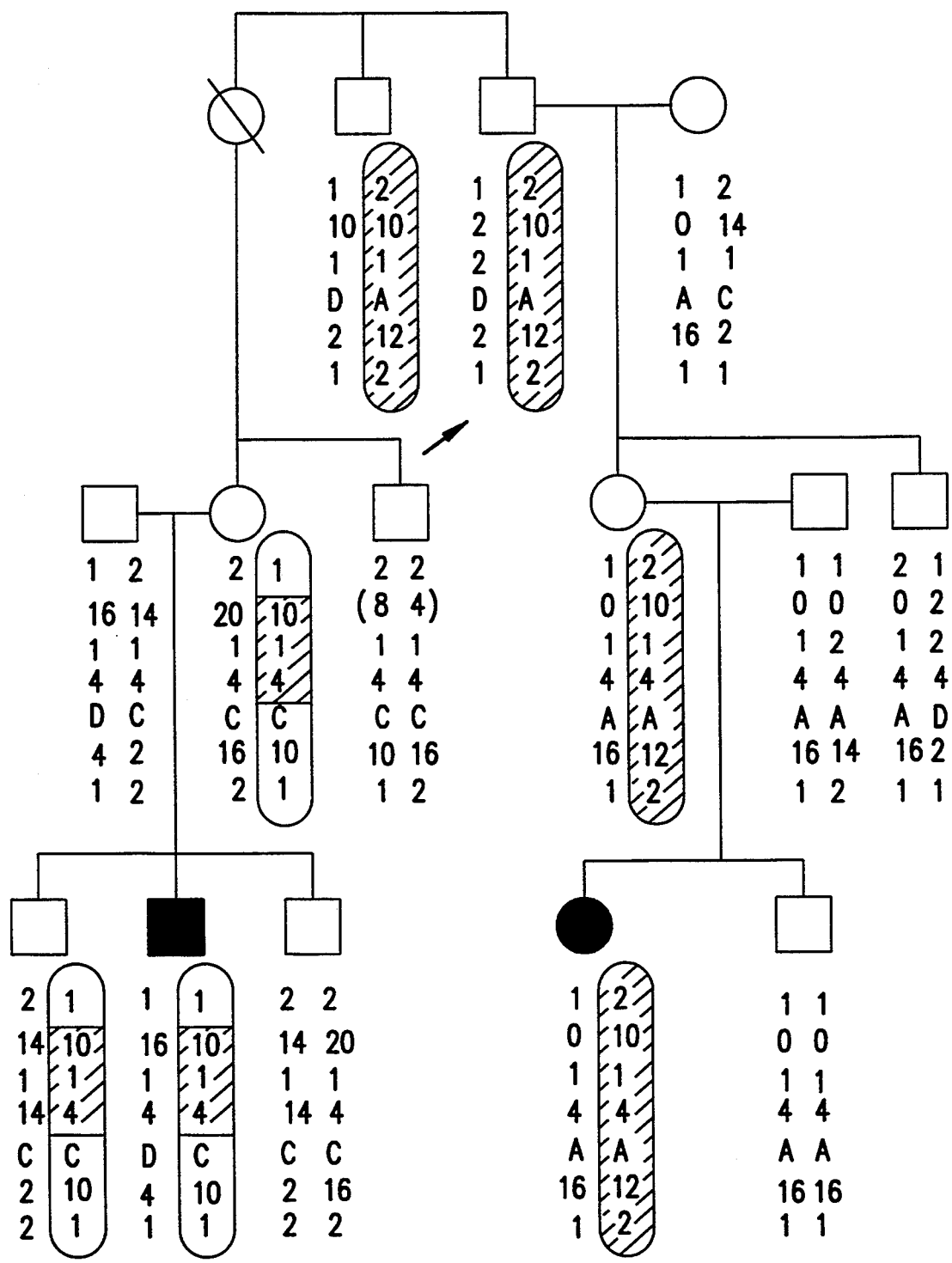
FIG. 5 shows the segregation of dystonia gene and marker alleles in a Jewish family.

In both non-Jewish and Jewish families with early onset dystonia, we have sought to define the location of the dystonia gene (DYT1) as precisely as possible. We expect that the same gene is involved in both types, but do not have firm proof for this conclusion yet. We have sought to maximize informativeness of marker probes in this region by screening genomic clones for (GT)n repeat sequences. By hybridizing digests of these clones with labeled (GT)n oligonucleotides, (GT)n repeats have been identified in clones for GSN, ASS, ABL, HXB and DBH. For the first three of these, we have sequenced flanking regions, prepared primer sequences and carried out PCR amplification in all members of the early onset pedigrees. The (GT)n repeat in GSN defines 13 alleles (PIG 0.76); in ASS, 9 alleles (PIC 0.83), in ABL, 9 alleles (PIC 0.64), and in HXB, 7 alleles (PIC to be determined). Several obligate recombinations have been observed between the GSN and HXB loci and the dystonia gene in Jewish families. In one of these families recombination events occurred between AK1 and ASS, and between ASS and D9S7 (126.3), with the dystonia gene segregating with ASS (FIG. 4). An apparent recombination has also been observed in a Jewish family between ASS and AK1 with the dystonia gene segregating all AK1 (FIG. 5). This information places the disease gene in a less than 6 cM interval between AK1 and ASS; the position of the ABL locus in this interval is not yet precisely defined.

In the course of defining the location of the DYT1 gene, we have also excluded the only two known candidate genes in this region, GSN and DBH with five subtypes of hereditary dystonia (Schuback et al.). GSN is excluded by virtue of 4 obligate recombinations between it and the dystonia gene in Jewish families. Alleles for DBH have been defined by two variable restriction sites -XbaI and TaqI (Schuback, D. E., et al., Nucleic Acids Res. 18:387 (1990)). The DBH locus shows an obligate recombination with the dystonia gene in families with early-onset dystonia, of both Jewish and non-Jewish types, Swedish myodonic dystonia and autosomal dopa-responsive dystonia.

b) Allele association

Allelic association, or linkage disequilibrium, refers to the tendency of specific alleles for different marker loci within a tightly linked group to occur together more frequently than would be expected by chance. Ordinarily, one expects that alleles at linked loci will be in equilibrium; that is, the frequency of any particular set of alleles (or haplotype) will be the product of their individual population frequencies. The cause for disequilibrium is often unclear. It can be due to selection for certain allele combinations, or to recent admixture of genetically heterogeneous populations. In addition, in the case of markers that are very tightly linked to a disease gene, an association of an allele (or group of linked alleles) with the disease gene is expected if the disease is due to a single mutation, which occurred in the recent past, so that sufficient time has not elapsed for equilibrium to be achieved through recombination events in that small chromosomal region. Studies of other hereditary diseases (e.g., cystic fibrosis) indicate significant allele associations for DNA sequences within 500 kb of the disease gene.

As the genetic distance between markers and the disease gene shortens, the usefulness of linkage analysis in defining the gene location declines because of the unlikely event of observing recombinants within such a small region (less than 2 cM). Allelic associations between genes within a small chromosomal region are useful in identifying markers that are closer to the disease gene than can be ascertained by linkage analysis. Because it is likely that the same mutation underlies the majority of cases of early-onset dystonia in the Ashkenazi population, one would expect a very strong association near the mutant gene site, provided the gene is not unusually large, and the mutation occurred or was introduced in the last two to three thousand years.

Figure 6:
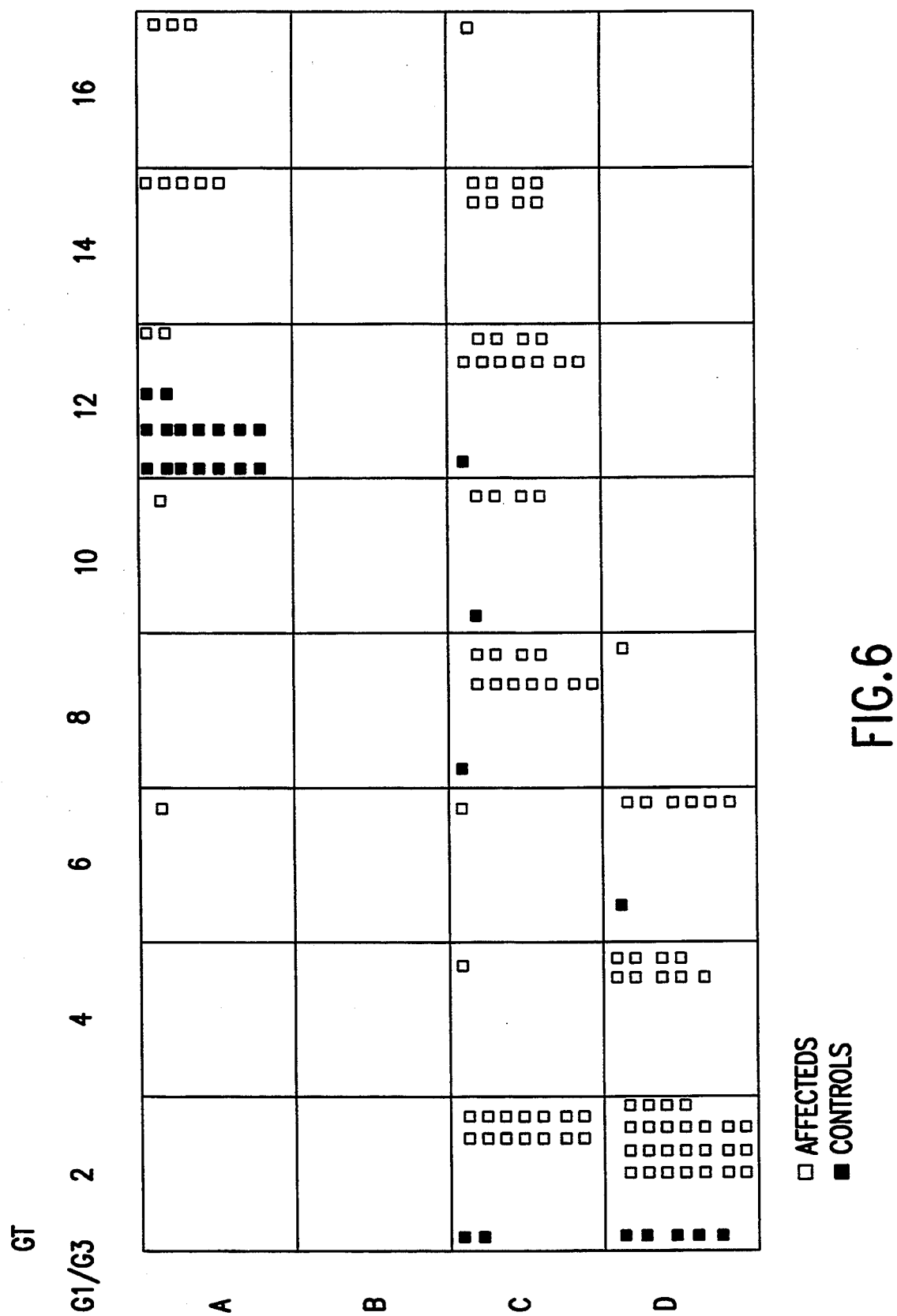
FIG. 6 shows the distribution of ASS haplotypes in the control and affected Ashkenazi populations (control chromosomes include 76 from 38 control individuals and the non-disease bearing chromosomes in 27 affected individuals).

The haplotype status of three polymorphic markers within the ASS locus in affected and control Jewish individuals have been determined (FIG. 6). Two alleles were defined by each of two conventional RFLPs, and 8 alleles were defined by a (GT)n repeat for ASS, which resulted in 32 different possible halotypes, of which 17 were observed in this population sample. A total of 94 control chromosomes and 79 disease chromosomes were analyzed. Of the control chromosomes, 103 could be phased by determining the parental chromosome contributing the alleles; of the disease-bearing chromosomes, 27 could be phased. A dramatic association between one of the ASS lialotypes, A12, and the dystonia gene was observed. About 60% of affected individuals bore the A12 haplotype associated with the dystonia gene; in contrast, only about 1% of normal individuals (with no family history of dystonia) bore this haplotype. The relative linkage disequilibrium (which is the ratio of the observed linkage disequilibrium, $\Delta$, over the maximum disequilibrium, $\Delta_{max}$, given the allele frequencies in the population) is equal to 0.578 (total disequilibrium would be equal to 1.0) (Thomson, 1981; Chakravarti et al., 1984). The Chi$^2$=42.1 (with 2 degree of freedom); p<<0.0001. This strong association of a particular ASS haplotype and the Jewish dystonia gene suggests that the two loci are within 500 kb of each other. Such a distance can be spanned with 5 genomic clones and is predicted to contain about 10 genes. We have begun isolating new genomic clones which are in this region by using clones for ASS to screen genomic libraries prepared from a somatic cell hybrid containing 9q as its only human chromosome.

It is also noted that the markers are used for identifying "sporadic" Jewish cases. These cases showed the same allele frequency as "familial." Most of the sporadic individuals in this population were hereditary. Thus, the markers are useful even for isolated Jewish cases.

Heterogeneity of dystonia a) Dystonia gene on 9q34

Figure 7:
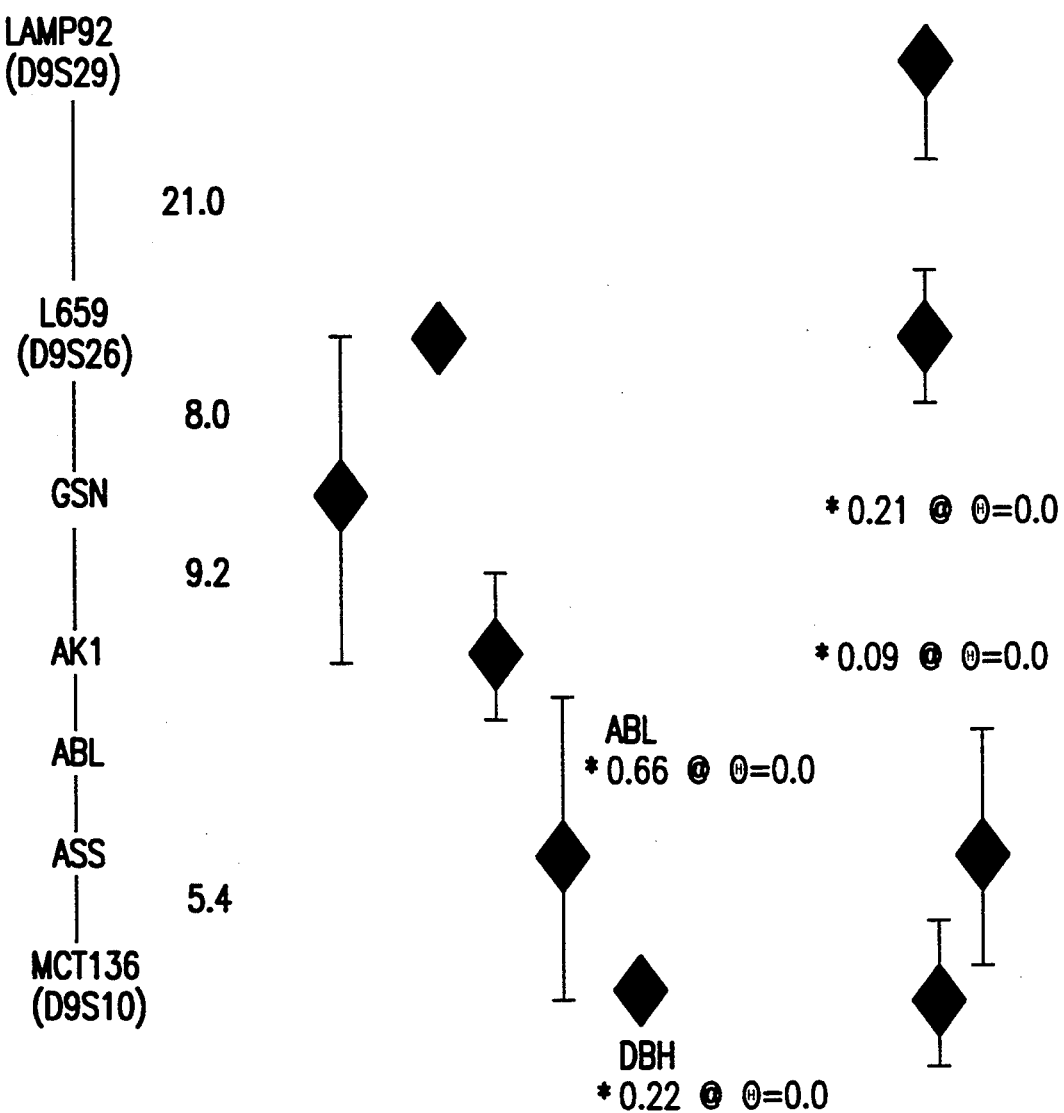
FIG. 7 shows areas in 9q31-34 excluded for dystonia in other clinical subtypes.

We have carried out two-point linkage analysis in several other hereditary forms of dystonia to determine if the disease gene is in this location (Table 3). Although data has been inconclusive, lod scores in the 9q34 chromosomal region tend to be positive in a Swedish family with late-onset dystonia (Swed-LO). Preliminary data on a non-Jewish family (Faro PG) with early-onset dystonia (32 members, 3 affected) also suggests that the disease gene may be in this region. In contrast, the 9q34 region has been excluded as bearing the dystonia gene in a South (So.) Swedish, alcohol-responsive, myodonic dystonia family (40 members, 19 affected) and in one autosomal dopa-responsive dystonia family ((Family S or Fam Sam; 110 members, 9 affected) (FIG. 7). Linkage data on a family (Fam DT) with early-onset dystonia, accompanied in same cases by mental retardation and developmental delay (31 members, 6 affected), also appears to exclude a disease gene in the 9q34 region, as does data on an American Family (Faro SM) with alcohol-responsive myodonic dystonia (20 members, 7 affected).

b) Dystonia gene on 11q22-q34

Occasionally during evolution, chromosomal regions were duplicated, moved to other chromosomes, and went on to evolve a set of different, but related, genes. Similarities in genes on 9q34 and 11q22-q34 were noted. For example, genes for tuberous sclerosis map to these two chromosome regions in different families, and there is a pseudogene for ASS on 11q, while the active gene is on 9q. It was reasoned that there might be a related dystonia gene in this region of 11q and has tested 9 polymorphic markers in that region in five families with hereditary dystonia which did not appear to map to 9q34 (Table 4).

Strongly suggestive evidence for linkage was observed for an American family with myoclonic dystonia (Fam Sm, same as Fam SM). Specifically, two-point linkage analysis with one 11q marker, phi2-22, gave a maximum lod score of 2.27 at a recombination value ($\theta$) of 0.0; similar analysis with a second marker, p2-7-1D6, approximately 15 cM centromeric to the first resulted in a maximum lod score of 1.79 at $\theta$=0.0. Multipoint analysis, using these two markers and dystonia, gave a maximum lod score of 2.40 across the entire 15 cM interval. Although this does not reach the statistically significant level denoted traditionally by a lod score >3.0, odds for linkage with dystonia in this region are 252:1, which certainly warrants additional attention to this region of 11q. Further, two-point linkage analysis in another American family (Fam DT) also gave a somewhat positive score, 0.81, with marker phi2-22 and the disease gene. However, the symptomatically similar, alcohol-responsive, myoclonic dystonia family from Sweden (Swed-myo) excludes linkage with this marker.

Radiation hybrids

Somatic cell hybrids containing only portions of human 9q are critical in cloning genomic DNA from this region and mapping cloned sequences to it. Two sets of radiation hybrids have been generated. We have characterized genes retained on this latter set of hybrids by Southern blot hybridization and PCR amplification (Table 5). All hybrids and the parental line lack the Lamp92 locus, suggesting it may be the site of insertion of the selectable hisD marker gene. Different hybrids retain varying lengths of 9q toward the telomere and will allow placement of new clones within known intervals.

TABLE 2

Lymphoblast lines established for genetic studies of dystonia

| Type | Ethnic Group | 1990 | Total | Families Collected | Source |
|---|---|---|---|---|---|
| Generalized- Focal | Jewish USA | 101[1] | >340 | 56 | Fahn |
| Generalized- Focal | non-Jewish USA | 120 | >265 | 12 | Fahn, McKusick, Adler, Kolodny |
| Focal- generalized | Sweden | 3 | 60 | 1 | Holmgren |
| Autosomal, dopa-responsive with Parkinson | USA | — | 62 | 1 | Fahn Nygaard |
| Myoclonus, alcohol-responsive | Sweden and USA | 1 | 74 | 5 | Wahlstrom Holmgren, Kurland, Fink, Fahn |
| Paroxysmal | USA | — | 8 | 1 | Kurland |
| With ataxia telangiocetaxia | Spain | 3 | 9 | 3 | de Yebenes |
| Torticollis | USA | 10 | 10 | 4 | Duane |
| X-linked, dopa-responsive with Parkinson | Philippines | 5 | 5 | 1 | Fahn |
| 9q34 deletion with nail patella and developmental delay | USA | 3 | 3 | 1 | La Cassie |
| 9q34:3p26 translocation with | USA | 5 | 5 | 1 | Mikati |

TABLE 2-continued

Lymphoblast lines established for genetic studies of dystonia

| Type | Ethnic Group | 1990 | Total | Families Collected | Source |
|---|---|---|---|---|---|
| hemiparaplegia | | | | | |

[1] Includes 17 single affected, Jewish, and 10 control, Jewish individuals, and a number of redrawn samples for the same individuals.

TABLE 3

Results of pairwise linkage analyses of dystonia (DYT1) with markers on chromosomes 9q

| Gene Symbol | Probe | Enzyme | Lod score at theta = | | | | | |
|---|---|---|---|---|---|---|---|---|
| | | | .000 | .05 | .10 | .20 | .30 | .40 |
| CHROMOSOME 9q | | | | | | | | |
| D9S26 | L659 | Taq | | | | | | |
| | 1) Fam R | | −1.72 | 0.89 | 1.03 | 0.95 | 0.67 | 0.29 |
| | 2) Jewish | | −1.38 | 0.35 | 0.46 | 0.41 | 0.26 | 0.11 |
| | 3) Swed-LO | | −0.01 | −0.03 | −0.05 | −0.07 | −0.06 | −0.02 |
| | 4) Swed-myo | | −2.62 | −0.71 | −0.42 | −0.16 | −0.04 | 0.00 |
| | 5) Fam DT | | 0.12 | 0.11 | 0.09 | 0.06 | 0.03 | 0.01 |
| | p31 | GT | | | | | | |
| | 1) Fam R | repeats | 0.24 | 3.03 | 2.99 | 2.50 | 1.71 | 0.71 |
| | 2) Jewish | | −9.28 | −0.19 | 0.53 | 0.74 | 0.50 | 0.20 |
| GSN | GT repeats | | | | | | | |
| | 1) Fam R | | 3.99 | 3.73 | 3.45 | 2.76 | 1.92 | 0.91 |
| | 2) Jewish | | −8.77 | 0.68 | 1.31 | 1.37 | 0.97 | 0.47 |
| | 3) Swed-LO | | −0.30 | −0.24 | −0.17 | −0.06 | −0.02 | 0.00 |
| | 4) Swed-myo | | −7.41 | −2.76 | −1.80 | −0.97 | −0.56 | −0.24 |
| | 5) Fam DT | | 0.22 | 0.17 | 0.13 | 0.06 | 0.02 | 0.00 |
| AK1 | | Taq/Ban | | | | | | |
| | 1) Fam R | | −0.12 | 0.00 | 0.04 | 0.04 | 0.03 | 0.01 |
| | 2) Jewish | | −6.48 | −0.72 | −0.02 | 0.28 | 0.18 | 0.04 |
| | 3) Swed-LO | | 0.47 | 0.41 | 0.35 | 0.22 | 0.11 | 0.03 |
| | 4) Swed-myo | | −3.37 | −1.78 | −1.22 | −0.68 | −0.38 | −0.17 |
| | 5) Fam DT | | −0.49 | −0.38 | −0.30 | −0.16 | −0.07 | −0.02 |
| ABL | GT repeats | | | | | | | |
| | 1) Fam R | | 5.11 | 5.06 | 4.78 | 3.91 | 2.72 | 1.27 |
| | 2) Jewish | | 1.33 | 1.19 | 1.06 | 0.80 | 0.55 | 0.29 |
| | 3) Swed-LO | | 0.14 | 0.14 | 0.12 | 0.07 | 0.02 | 0.00 |
| | 4) Swed-myo | | 0.12 | 0.11 | 0.08 | 0.05 | 0.02 | 0.01 |
| | 5) Fam DT | | no data | | | | | |
| | 6) Fam PG | | 0.75 | 0.67 | 0.57 | 0.37 | 0.18 | 0.03 |
| ASS | GT repeats | | | | | | | |
| | 1) Fam R | | 4.65 | 4.58 | 4.36 | 3.59 | 2.50 | 1.15 |
| | 2) Jewish | | 3.60 | 4.72 | 4.24 | 3.03 | 1.80 | 0.76 |
| | 3) Swed-LO | | 0.58 | 0.51 | 0.44 | 0.30 | 0.17 | 0.06 |
| | 4) Swed-myo | | −8.26 | −3.57 | −2.32 | −1.16 | −0.57 | −0.21 |
| | 5) Fam DT | | −3.20 | −1.33 | −0.82 | −0.35 | −0.14 | −0.04 |
| | 6) Fam PG | | 0.87 | 0.79 | 0.70 | 0.49 | 0.26 | 0.07 |
| | 7) Fam SM | | −5.24 | −1.84 | −1.09 | −0.43 | −0.17 | −0.07 |
| D9S10 | MCT136 | Pst | | | | | | |
| | 1) Fam R | | −4.37 | 1.15 | 1.44 | 1.37 | 0.96 | 0.38 |
| | 2) Jewish | | −3.26 | −1.04 | −0.47 | −0.07 | 0.01 | 0.00 |
| | 3) Swed-LO | | 0.60 | 0.68 | 0.65 | 0.48 | 0.26 | 0.07 |
| | 4) Swed-myo | | −2.41 | −1.43 | −0.82 | −0.29 | −0.08 | −0.01 |
| | 5) Fam DT | | −0.12 | −0.11 | −0.09 | −0.06 | −0.03 | −0.01 |
| DBH | DBH1.0 | Taq/Xba | | | | | | |
| | 1) Fam R | | −1.53 | 4.00 | 3.95 | 3.31 | 2.31 | 0.90 |
| | 2) Jewish | | −3.90 | 0.08 | 0.34 | 0.35 | 0.22 | 0.09 |
| | 3) Swed-LO | | −0.57 | −0.16 | 0.01 | 0.12 | 0.10 | 0.04 |
| | 4) Swed-myo | | −8.41 | −2.23 | −1.39 | −0.63 | −0.27 | −0.10 |
| | 5) Fam DT | | 0.40 | 0.34 | 0.28 | 0.17 | 0.08 | 0.02 |
| D927 | EFD126.3 | Msp | | | | | | |
| | 1) Fam R | | −14.43 | −5.45 | −3.26 | −1.22 | −0.36 | −0.08 |
| | 2) Jewish | | −18.27 | −4.88 | −2.97 | −1.20 | −0.41 | −0.07 |
| ABO | 1) Fam R | | −2.35 | 0.91 | 1.03 | 0.91 | 0.58 | 0.19 |

TABLE 4

Pairwise linkage analysis of DYT1 with markers on 11q

| Gene Symbol | Probe | Enzyme | Lod score at theta = | | | | | |
|---|---|---|---|---|---|---|---|---|
| | | | .000 | .05 | .10 | .20 | .30 | .40 |
| CHROMOSOME 11q | | | | | | | | |
| D11S85 | phi6−3 | Msp I | | | | | | |
| | 1) Fam SM | | −2.32 | 0.23 | 0.37 | 0.33 | 0.19 | 0.05 |

TABLE 4-continued

Pairwise linkage analysis of DYT1 with markers on 11q

| Gene Symbol | Probe | Enzyme | Lod score at theta = .000 | .05 | .10 | .20 | .30 | .40 |
|---|---|---|---|---|---|---|---|---|
| D11S84 | p2-7-1D6 | Taq | | | | | | |
| | 1) Fam Sm | | 1.79 | 1.60 | 1.41 | 1.01 | 0.61 | 0.24 |
| | 2) Fam Sam | | −7.20 | −2.26 | −1.62 | −0.87 | −0.43 | −0.18 |
| | 3) Swed-myo | | 0.04 | 0.04 | 0.03 | 0.03 | 0.03 | 0.02 |
| STYM | | Taq | | | | | | |
| | 1) Fam Sm | | 0.19 | 0.16 | 0.13 | 0.08 | 0.04 | 0.01 |
| D11S35 | phi2-22 | GT repeats | | | | | | |
| | 1) Fam Sm | | 2.27 | 2.07 | 1.86 | 1.41 | 0.93 | 0.41 |
| | 2) Fam Sam | | −5.56 | −1.04 | −0.58 | −0.25 | −0.14 | −0.07 |
| | 3) Swed-myo | | −8.67 | −2.24 | −1.19 | −0.30 | 0.02 | 0.08 |
| | 4) Fam K | | −0.01 | −0.01 | −0.01 | −0.01 | −0.01 | 0.00 |
| | 5) Fam DT | | 0.81 | 0.70 | 0.58 | | 0.36 | 0.17 |
| 0.04 | CJ52.208 | Msp | | | | | | |
| D11S351 | 1) Fam Sm | | 1.87 | 1.68 | 1.48 | 1.05 | 0.61 | 0.20 |
| D11S144 | MCT1'28.1 | Msp | | | | | | |
| | 1) Fam Sm | | 0.30 | 0.25 | 0.21 | 0.13 | 0.06 | 0.02 |
| | 2) Fam Sam | | −5.95 | −1.20 | −0.69 | −0.25 | −0.07 | −0.01 |
| | 3) Swed-myo | | −5.00 | −1.19 | −0.52 | −0.05 | 0.05 | 0.03 |
| D11S29 | L7 | Taq | | | | | | |
| | 1) Fam Sm | | 0.02 | 0.02 | 0.01 | 0.01 | 0.00 | 0.00 |
| | 2) Fam Sam | | 0.03 | 0.02 | 0.02 | 0.01 | 0.00 | 0.00 |
| | 3) Swed-myo | | −2.17 | −0.18 | 0.04 | 0.18 | 0.18 | 0.12 |
| D11S350 | pHHH172 | PvuII | | | | | | |
| | 1) Fam Sm | | 0.02 | 0.02 | 0.01 | 0.01 | 0.00 | 0.00 |
| D11S147 | pHB118 | Pst | | | | | | |
| | 1) Fam Sm | | no data | | | | | |
| | 2) Fam Sam | | −3.23 | −0.90 | −0.62 | −0.33 | −0.16 | −0.06 |
| | 3) Swed-myo | | −0.93 | −0.11 | 0.06 | 0.13 | 0.09 | 0.04 |

(Markers are given in order from centromere to qtelomere.)

TABLE 5

Region of human 9 retained in Dr. Jackson's radiation hybrids

| Hybrids[2] | loci[3]: MCT112 | GSN | ABL | ASS | MCT136 | EFD126.3 |
|---|---|---|---|---|---|---|
| A202 (3) | + | + | + | + | + | + |
| A505 (1) | + | + | + | + | + | (−) |
| B401 (3) | + | + | + | + | − | − |
| B505 (1) | + | + | + | − | − | − |
| B201 (3) | + | + | − | − | − | − |
| B202 (4) | − | − | − | − | − | − |

[2]Cloned hybrids prepared fusion of irradiated hybrid cells, containing only human chromosome 9 with a selectable marker (hisD) inserted in the q arm, to hamster line. Number in parentheses refers to number of hybrid clones which show the same distribution of loci.
[3]Loci are in order from centromere to 9qtr, left to right. Probes - MCT112, MCT136 and EFD126.3 were evaluated by Southern blot hybridization; loci - GSN, ABL and ASS by PCR amplification.

TABLE 6

Molecular Markers Useful in Molecular Diagnostics

| Probe | Locus | No. of Alleles | PIC Value |
|---|---|---|---|
| GSNGT | GSN | 13 | 0.76 |
| LAK1B3.25 | AK1 | 2 | 0.28 |
| ABLGT | ABL | 9 | 0.64 |
| ASSG1 | ASS | 2 | 0.25 |
| ASSG2 | ASS | 2 | 0.38 |
| ASSG3 | ASS | 2 | 0.50 |
| ASSGT | ASS | 9 | 0.83 |
| MCT136 | D9S10 | 2 | 0.37 |

Example 4

Highly informative (GT)n repeat polymorphisms (Litt et at, Am. J. Hum. Genet. 44:397–401 (1989); Weber et at, Am. J. Hum. Genet. 44:388–396 (1989)) have been used for several loci which lie between D9S26 and D9S10, including gelsolin (GSN) (Kwiatkowski (1991) et al, Nucl. Acids Res. 19:49676; the abl oncogene (ABL) (Kwiatkowski, D. (1991) supra.); and argininosuccinate synthetase (ASS) (Kwiatkowski (1991) et at, Am. J. Hum. Genet. 48:121–128, as well as RFLPs for the adenylate kinase-1 (AK1) gene (Beth-Hansen, (1989)et al., Nucleic Acid Res. 17:4004; Schubak et al., (1989) Neuron. 2:1427.–1434) to identify recombination events in the Jewish families that localize the DYT1 gene to a 6 cM region flanked by the AK1 and ASS loci. We have also evaluated allele association between DYT1 and alleles at ASS and ABL in the 12 original Ashkenazi families (Kramer et at, Ann. Neurol. 27:114–120 (1990)) and in an·additional 49 Ashkenazi affected and 42 control Ashkenazim. The combined data set yields significant evidence for allelic association between DYT1 and an extended haplotype at the ABL-ASS loci.

MATERIALS AND METHODS

Neurologic examination and family material

A series of 53 Ashkenazi Jewish individuals (from 52 families) affected with classic ITD were ascertained for this study from a computerized database file of patients followed by members of the Movement Disorder Group at Columbia Presbyterian Center (50 families) or through the Dystonia Medical Research Foundation (2 families). Clinical and pedigree information on these families has been reported in detail (Bressman et al.,

*Ann. Neurol.* 26:612-620 (1989)). The criteria for the diagnosis of primary versus secondary dystonia and the method of evaluation was the same as described previously (Bressman et al., *Ann. Neurol.* 26:612-620 (1989); Kramer et al., *Ann. Neurol.* 27:114-120 (1990)). Briefly, a neurological history and standardized examination were performed by a neurologist trained in analysis of movement disorders. Video examinations were performed according to a standardized protocol and reviewed by at least two neurologists who were blind to the status and identity of the subject. A final determination of definite, probable, or possible dystonia was made Bressman et al., *Ann. Neurol.* 26:612-620 (1989)); only individuals designated as definitely affected were classified as affected in this study.

The criteria for designation as Ashkenazi Jewish was the same as described (Bressman et at, *Ann. Neurol.* 26:612-620 (1989). In this study, 49/54 had 100% Ashkenazi Jewish ancestry, 2 individuals had 3/4 Ashkenazi Jewish grandparents, 2 had 2/4 Ashkenazi Jewish grandparents and 1 had only 1 Ashkenazi Jewish grandparent. There was no evidence for inheritance through the non-Ashkenazi ancestor in these latter 5 individuals.

Unrelated, unaffected individuals with 100% Ashkenazi Jewish ancestry and no family history of dystonia were included as controls. These came from three sources: spouses married into the dystonia families, but with no direct blood line to the affecteds (n=28), staff neurologists (n=11) and members of families in which some individuals were affected with familial dysautonomia (n=42). This latter disease is a rare, autosomal recessive neurologic disease in which classic cases appear only in the Ashkenazi Jewish population. Controls from the dysautonomia families manifested no dystonia symptoms, as evaluated by Dr. Felicia Axelrod (NYU Med. Ctr.). The other control subjects were evaluated using the same examination procedures as described above for affected individuals, except for 9 of the staff neurologists who did not have neurologic exams.

DNA methods, probes, and polymorphism analysis

Blood was obtained by venesection from consenting family members. DNA was extracted from lymphoblast lines (Anderson, et al., *In Vitro* 29:856-858 (1984); Breakefield, et al., *J. Neurogenet.* 3:159-175 (1986)). Southern blot analysis was carried out according to methods described previously (Ozelius et al., *Neuron* 24:1427-1434 (1989)). DNA probes were labeled with [32P]dATP (3000 Ci/mmol; Amersham) by random oligonucleotide priming (Feinberg et al., *Anal. Biochem.* 132:6-13 (1983)) and hybridized to filters as described in (Ozelius et al., *Neuron* 24:1427-1434 (1989)). Four RFLP marker probes on 9q were used: pMCT136 (PstI) for random VNTR locus D9S10 (q34) (Lathrop et al., *Am. J. Hum. Genet.* 42:498-505 (1988); lathrop et al., *Genomics* 3:361-366 (1988)); pAK1B3.25 (TaqI, BanI) for the AK1 locus (q32-34) (Beth-Hansen, et al., *Nucleic Acid Res.* 1:7:4004 (1989); Schuback et al., submitted; Zuffardi et al., *Hum. Genet.* 82:17-19 (1989)); and ASSG1 (HindIII) and ASSG3 (PstI) for the ASS locus (q34) (Northrup et al., *Genetics* 5:442-444 (1989)).

Analysis of allele status for the GSN, ABL, and. ASS GTn repeat polymorphisms was carried out on gertomit DNA using oligonucleotide primer pairs described elsewhere (Kwiatkowski, D. *Nucl. Acids Res.*, in press (1991); Kwiatkowski et al., *Nucl. Acids Res. supra.* (1991); Kwiatkowski et al., *Am. J. Hum. Genet.* 48:121-128 (1991)) in the polymerase chain reaction (PCR) to amplify the repeat-containing region. Reaction volumes were 10 ul and contained 0.2 mM dATP, dCTP, dTTP; 2.5 uM dGTP; 4 ng each oligonucleotide; 0.80 ul $^{32}$p dGTP (3,000 mCi/mm); 0.05 ul Taq polymerase and 1× reaction buffer (Perkin-Elmer Cetus). Thermal controller settings were 94° C. for 1.5 rain; 25 cycles of 94° C. for 1 min, 55° C. for 1 min, and 72° C. for 1 min; 72° C for 10 min. Amplified products were analyzed and exposed as described in Kwiatkowski et al., ( 1991 ), supra.

Statistical Methods

A common measure of the strength of an association between a disease and a particular marker allele is the odds ratio. An odds ratio significantly greater than 1.0 indicates that the particular allele under consideration is more frequent in patients, compared to controls; whereas a ratio less than 1.0 indicates a decreased frequency among patients. The significance of an odds ratio is measured by a $X^2$ test. The association between the DYT1 gene and alleles at closely linked loci were examined according to the methods for calculating odds ratios described in Fleiss, J. L. *Statistical methods for rates and proportions*, John Wiley and Sons, New York (1981) and Thomson, G. *Theoretical Population Biology* 20:168-208 (1981). We considered one system at each of four marker loci: the (GT)n polymorphisms at ASS and ABL, and the RFLPs at AK1 and D9S10. Our initial sample comprised 13 affected individuals and 16 unrelated, normal, Ashkenazi individuals from the original families on which our linkage studies were based (Kramer et al., *Ann. Neurol.* 27:114-120 (1990)). This odds ratio analysis does not require knowledge of linkage phase for affected individuals; and is thus, a preliminary analysis of allelic association because normal chromosomes are combined with disease allele bearing chromosomes; among the affected group.

More rigorous allelic association analysis, according to methods described in Chakravarti et al., *Amer. J. Hum. Genet.* 36:1239-1258 (1984) was done with those markers for which the odds ratio suggested evidence of an association with DYT1. We considered the (GT)n polymorphism at ABL, and a three-system haplotype at ASS; specifically, eight alleles are defined by the (GT)n, and two alleles are defined by each of the two RFLPs, for a total of 32 possible tnaplotypes at ASS. Our sample was enlarged to include 53 affected individuals and 81 controls. For this analysis, alldes (or haplotypes, as for ASS) at linked markers on disease-bearing chromosomes from affected individuals, were compared to those on non-disease chromosomes from controls. Of the 53 affecteds, we were able to unambiguously deduce disease-bearing chromosome in 26 individuals. Among controls, we could haplotype 73 individuals. Thus, the analysis for ASS is based on a sample of 26 disease-bearing chromosomes and 146 control chromosomes.

Marker allele frequencies were estimated by simple gene counting in the control sample. The presence of significant allelic association was tested using a $X^2$ test of homogeneity (described in Chakravarti et al., *Amer. J. Hum. Genet.* 36:1239-1258 (1984) and applied in Kerem et al., *Science* 245:1073-1080 (1989). The degree of association was measured by relative linkage disequilibrium,, or D', described in Thomson, G. *Theoretical Population Biology* 20:168-208 (1981) and Chakravarti et al., *Amer. J. Hum. Genet.* 36:1239-1258 (1984).

A panel of 62 Venezuelan reference pedigrees (Haines et al., 1990) containing over 700 individuals was used to construct a linkage map of the critical area on chromosome 9q32-34 containing the markers D9S26 (L659), GSN, AK1, ABL, ASS, D9S10 (MCT136) and D9S7 (EFD126.3) (Ozelius et al., unpublished data). All data were entered into a computer file using the L1PIN data management program (Troffater et al., 1986). Analysis was performed using the MAPMAKER program (version 1.0) Lander et al., *Genomics* 1:174–181 (1987), employing the strategy described in Haines et al., *Genomic,*, 8:1–6 (1990).

RESULTS

Crossover Events

Figure 8:
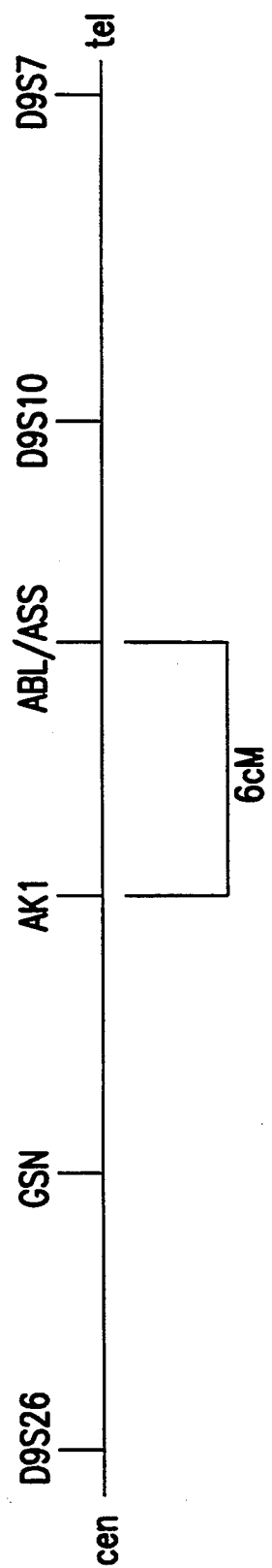
FIG. 8 are markers in the q32-q34 region of chromosome 9.

The order of markers in the q32-q34 region of chromosome 9' is shown in FIG. 8. The chromosomal order as well as the genetic distance between markers was determined using 62 Venezuelan reference pedigrees. Loci were placed at the given positions with odds of at least 200:1 over any other position in the map (Ozelius et al., unpublished data). The order for ABL and ASS could not be determined because only one recombination was seen between these markers in this data set. Based on in situ hybridization results with a chronic mylogenous leukemia (CML) cell line (BV173; Hooberman et al., *Blood* 74:1073–1080 (1989), ABL is centromeric to ASS (T. Lerner, MGH-East, personal communication). (GT)n polymorphisms at the GSN, A33L and ASS loci, as well as RFLPs at AK1 and at D9S10, were used to score obligate recombination events between these loci and the DYT1 gene in affected individuals in Ashkenazi Jewish families. In the 12 families previously described Kramer et at, *Ann. Neurol.* 27:114–120 (1990), we observed 5,1,0 and 2 obligate crossovers with GSN, AK1, ABL, and D9S10, respectively as well as a probable crossover at ASS. Two point lod scores and multipoint analysis presented in Kwiatkowski et al., *Amer. J. Hum. Genet.* (in press) support these results showing that the most likely position for the DYT1 gene is midway between AK1 and ASS with a lod score of 4.43 at 0=0.

Figure 9:
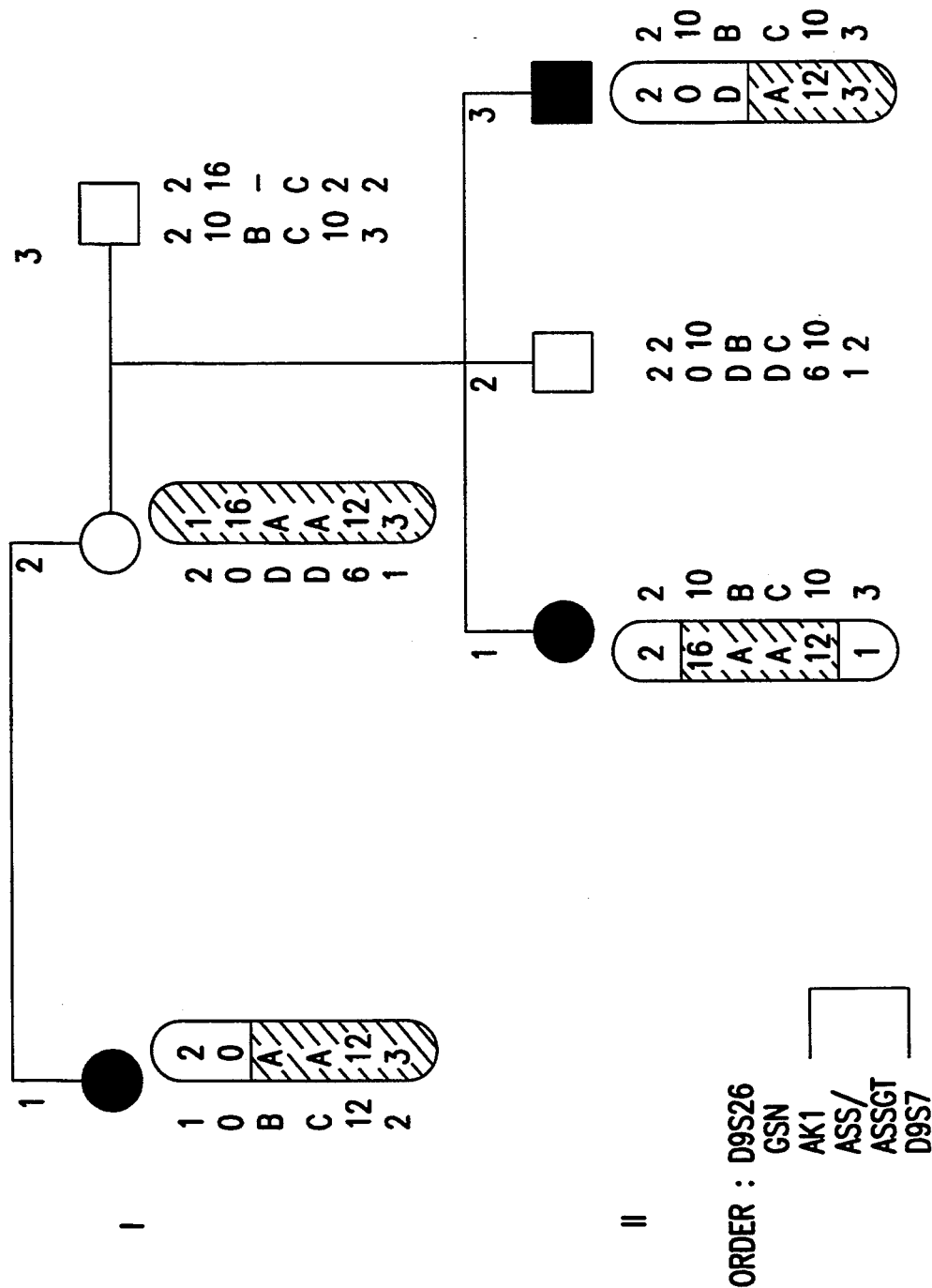
FIG. 9 is a Jewish pedigree in which several recombination events have occurred.
Figure 10:
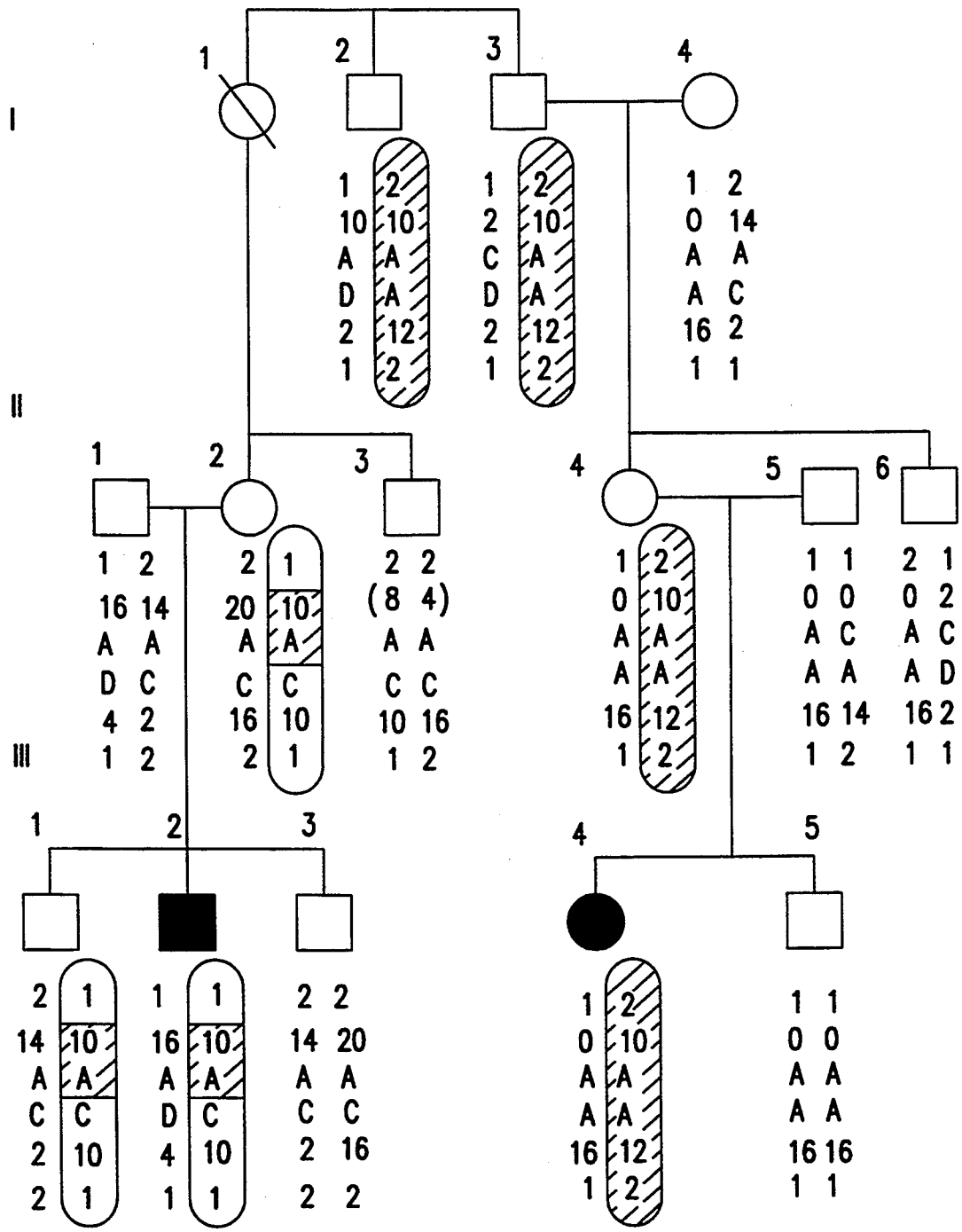
FIG. 10 is a probable crossover event which places the disease gene proximal to ASS.

FIG. 9 shows a Jewish pedigree in which several recombination events have occurred. The most relevant for determining the position of the disease gene is in individual 11-3. This cross occurs between AK1 and ASS on the disease chromosome (the ABL polymorphism is uninformative) and it places the disease gene distal to AK1. FIG. 10 shows a "probable" crossover event which places the disease gene proximal to ASS. In this case, affected members III-2 and III-4 do not share a common haplotype at the ASS locus (again the ABL polymorphism is uninformative). The cross itself appears to have occurred in an individual two or three generations preceding the affected individuals. It cannot be ruled out that two different disease genes, associated with different ASS haplotype (A12 and CIO), have entered from two different branches of the family and that no crossover occurred in the family. However, because there is no family history of dystonia in any of the married-in individuals in this family and the incidence of the disease gene in this population is 1/15,000, this possibility is unlikely. Using the Venezuelan pedigrees, the distance between AK1 and ASS was calculated to be 6 cM (FIG. 8); the DYT1 gene thus lies within this interval.

Allelic association

We calculated odds ratios as preliminary measures of association between DYT1 and four closely linked markers: ABL, ASS, AK1 and D9S10. As described in the Statistical Methods section, for the initial sample we selected one affected individual (generally the proband) from each of the 12 original Jewish families on which our linkage results were based (Kramer et al., 1990). However, in the family which represents a "probable" crossover event between ASS and DYTI. (FIG. 10) we included both affected members (III-2; 111–4). This resulted in a sample of 13 affected individuals. The control sample consisted of 16 Ashkenazim from the original families, unrelated by blood to any affected member, or to each other. Of the 26 ASS (GT)n alleles represented among the affected individuals, 12 were allele "12" (106 bps using :primers described in Kwiatkowski et al., *Am. J. Hum. Genet.* 48:121–128 (1991); whereas in controls only 2 of the 32 ASS alleles were "12". The odds ratio is 12.86 ($X^2 = 10.39$, $p < 0.008$). Of the 26 ABL alleles among affected individuals, 22 were allele "4" (141 bps using primers in Kwiatkowski et al., *Nucl. Acids. Res.* 19:4967 (1991), compared with 19 of the 32 control alleles. The corresponding odds ratio is 3.76 ($X^2 = 3.28, 0.10 < p < 0.05$). There was no evidence for an association between DYT1 and any of the alleles at AK1 or D9810. The highest $X^2$ obtained was 0.73 and 1.0, respectively.

The nonrandom association between DYT1 and alleles at ASS and ABL, warranted collection of additional families. In all, 53 affected individuals from 52 unrelated families and 81 controls were typed for the three polymorphisms at ASS and for the (GT')n polymorphism at ABL. Of the 53 affected individuals, 38 could be haplotyped at ASS; of these, the disease-bearing chromosome could be identified in 26. Of the 81 control individuals, 73 could be haplotyped at ASS. Thus, for this analysis the sample consisted of 26 disease-bearing and 146 control chromosomes.

Figure 11:
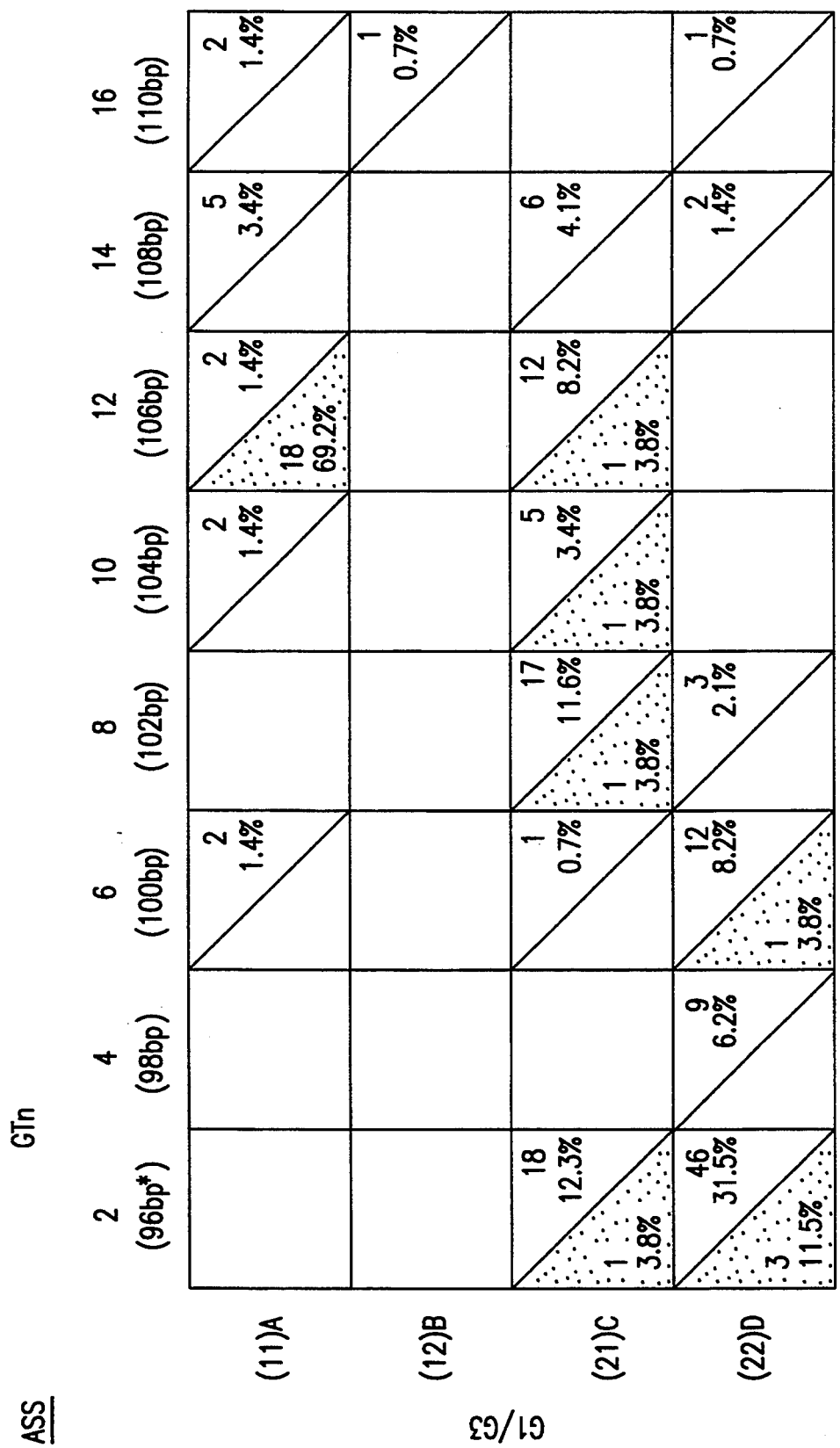
FIG. 11 is haplotypes at ABL-ASS.

The distribution of ASS haplotypes in control and affected chromosomes is illustrated in FIG. 11. Among the affecteds, 18 of the 26 chromosomes (69%) bore the "A 12" haplotype, whereas only 1.4% of control chromosomes had this haplotype. This is remarkably significant, indicated by a $X^2 = 92.53$, $p << 0.001$. The relative linkage disequilibrium, or D', is equal to 0.688.

For ABL, we could identify the disease-bearing chromosome in 26 of the original 53 affected individuals. The control group consisted of 81 individuals (162 chromosomes). Of the 26 affected chromosomes, 24 chromosomes (92%) carried the "4" allele; of the 162 control chromosomes, 102(63%) carried the "4" allele. The $X^2$ value for the difference between affected and controls is 7.44, $p < 0.01$. This is not as significant as the results for ASS; however, this is to be expected, since the "12" allele at ASS is very rare, whereas the "4" allele at ABL is very common in the Ashkenazi population, this could also indicate that ABL is farther from DYT1 than is ASS or that a recombination event took place shortly after the mutation occurred.

We then constructed haplotypes with both ABL and ASS markers, and examined allelic association between DYT1 and the "4/A 12" haplotype. Of those chromosomes for which linkage phase could be determined, 69% of affecteds (18 of 26) carried the "4/A12" haplotype; only 0.75% of controls (1 of 134) carried the "4/A12". These gave values of $X^2 = 91.07$, $p << 0.001$, and D'=0,686.

Sporadic ITD

Of the 53 affecteds who were typed, 13 were classified as sporadic cases with no family history of dystonia. These were collected as singleton cases and therefore phase not be determined. In the sporadic cases we were also unable to determine disease bearing chromosome, however, we were able to tabulate the number of cases who potentially had an "A 12" haplotype at the ASS locus on one of their chromosomes versus a "non A12" haplotype on either chromosome, and to compare this to the definitely familial group. Sixty-two percent of the sporadics (8/13) could carry an "A 12" allele on one chromosome, while 38% (5/13) definitely did not carry an "A12" on either chromosome "non-A12"). This compares to 70% (28/40) "A 12" and 30% (12/40) "non-A 12" in the familial group. The numbers are not significantly different, suggesting that most sporadic cases are probably hereditary.

DISCUSSION

We have identified recombination events in Ashkenazi Jewish families which confirm and extend the linkage data previously reported Ozelius et al., Neuron 2:1427–1434 (1989); Kramer et al., Ann. Neurol. 27:114–120 (1990). These crossover events place the DYT1 gene within a 6 cM region flanked by AK1 and ASS. We also report strong linkage disequilibrium with a particular extended haplotype based on the ABL and ASS markers ($X^2=91.07$). These results suggest that the DYT1 gene is closer to the ASS end of this 6 cM interval (more telomeric). In light of linkage disequilibrium results in cystic fibrosis Kerem et al., Science 245:1073–1080 (1989) and Friedreich ataxia Fujita et al., Proc. Natl. Acad. Sci. USA 87:1796–1800 (1990), this would suggest that the DYT1 gene is within 500 kb–1 Mb of the ABL and ASS loci. However, the distance between the disease gene and these marker loci may be physically larger because the DYT1 mutation may not be as old as the most common cystic fibrosis or Friedreich ataxia mutations. The very likely recombination between ASS and the disease gene seen in FIG. 10 would support this idea, as would the fact that no linkage disequilibrium is seen between the ABL and ASS polymorphisms on control Jewish chromosomes. In order to be associated with a particular haplotype C4/A 12"), the most common DYT1 mutation in this population must have occurred more recently than the polymorphisms at the ABL and ASS loci, indicating that its high degree of association with the marker loci may be due in part to the relatively recent occurrence of the mutation in the Ashkenazi Jewish population. Together, these data suggest the distance between the ABLASS loci and the DYT1 gene may be more than 1 M6.

We eliminated several individuals from the linkage disequilibrium analysis because either the phase at their ASS haplotype (16 of 53 affecteds and 8 of 81 controls) or the disease-bearing chromosome (11 of 53 affecteds) could not be determined. The ambiguity in phasing derived from those individuals who were heterozygous for both the HindIII and PstI RFLPs at ASS; i.e., it was not clear whether these individuals were in coupling or repulsion phase. Some concern may arise from the potential bias in our allelic association results due to eliminating these individuals. In fact, only one of the eight "unphaseable" controls could have been "A12", i.e. was heterozygous at both RFLPs and carried at least one "12" allele at the (GT)n polymorphism. On the other hand, 10 of the 16 "unphaseable" affecteds could have been "A12". Of the 11 for which the disease-bearing chromosome could not be determined, 6 definitely had the "A12" haplotype on one of their chromosomes. Even if the one control is actually "A12", and none of the affecteds are "A12" on their disease-bearing chromosome, the allelic association between DYT1 and the "A12" haplotype would still be highly significant ($X^2=39.59$, p<0.008).

Haplotypes at ABL-ASS could be determined for 26 disease-bearing chromosomes (FIG. 11); of these, 18 were ".4/A 12" while the other 8 had various allele combinations. With the exception of the haplotypes "6/C8" and "-12/D2" in the table, all the "non-4/A12" haplotypes can be derived from single crossover events between ABL and relatively common ASS haplotypes in the control population. However, because the numbers are so small, and since the ABL "4" allele is so common in the population, it is difficult to know whether these "non-4/A 12" haplotypes represent different mutations or crossover events. The possibility that some of the "non-4/A12" haplotypes are different mutations will be investigated by looking at various phenotypic and demographic differences between the "4/A12" individuals and the "non-4/A12" cases. Site of onset, physical distribution of symptoms (i.e. focal, segmental, generalized), geographic origin, and age-at-onset will he used to assess potential genetic heterogeneity. If in fact the "non-4/A 12" haplotypes represent crossover events, then examination of these chromosomes with additional markers in the region should further pinpoint the disease gene within this region.

The percentage of sporadic cases which appear to have an "A12" haplotype is not significantly different from the percentage of familial cases with this haplotype. This suggests that most sporadic cases actually have heritable dystonia with a lack of family history due to low penetrance (30%) in this population and variable expressivity, whereby mild signs may go undiagnosed and lends support to the idea that most cases of dystonia in the Ashkenazi Jews have arisen from a single mutation as was predicted by a segregation analysis study done on this population Risch et al., Am. J. Hum. Genet. 46:533–538 (1990). It also suggests that in this population the gene frequency is at least two-fold higher than previously thought and that the penetrance is lower. The haplotype data at ASS also confirms the other major conclusion made in several segregation analysis studies; i.e. MD is inherited as an autosomal dominant trait in the Ashkenazi Jewish population Zilber et al., J. Med. Genet. 21:13–20 (1984); Bressman et al., Ann. Neurol 26:612–620 (1989); Pauls et al., Neurology, 40:1107–1110 (1990); Risch et al., Am. J. Hum. Genet. 46:533–538 (1990). Of the 53 affected individuals typed at ASS, 48(90.6%) were heterozygous for this haplotype while 5(9.4%) were homozygous. This result is consistent with dominant inheritance of the disease gene and strongly rejects recessive inheritance, which would have yielded far more homozygotes.

The ABL-ASS haplotype has predictive value for the disease state that will not only be helpful for molecular diagnosis and genetic counseling, but also allow a better clinical definition of the MD phenotype. By consensus, overt twisting movements or postures are accepted as part of the dystonia spectrum Fahn et al., Classification and investigation of dystonia. In Movement disorders 2 332–358 (Marsden and Fahn Eds.) (1987). But clinical observations in "obligate carriers" have led to the consideration of certain common non-dystonic features, such as tremor (Zilber et al., J. Med. Genet. 21:13–20 (1984); Fletcher et al., Brain 113:379–395 (1990)) and stuttering (Zilber et al., J. Med. Genet. 21:13–20 (1984)) as formes frustes or mild expression of the dystonia gene. We can now identify carriers of the DYT1 gene in some Jewish families and evaluate an increased incidence of certain mild neurologic symptoms. This analysis can be extended to examine environmental factors which may modify clinical symptoms.

This finding of linkage disequilibrium between the DYT1 gene and the ABL-ASS extended haplotype has allowed us to narrow the region containing the disease gene from 30 cM to 1-2 cM. We are generating more markers in this region by walking from the ends of the ABL and ASS loci. We plan to assess linkage disequilibrium between these markers and the disease gene by finding (GT)n polymorphisms for each new marker.

The information presented above is consistent with a single mutation causing most cases of dystonia in the Ashkenazi Jewish population. The "non-A12" haplotypes seen in some affecteds, may represent evolutionary recombinations between the disease gene and the background haplotype C4/A12") on which the original mutation occurred, or may indicate other mutations. An extended haplotype encompassing additional markers in this region will enable us to locate historical recombination events within this region, and thus allow more precise localization of the DYT1 gene, and some idea of when the mutation occurred in history.

---

We claim:

1. A method for detecting the presence of a haplotype which is predictive for determining the presence of a gene linked with torsion dystonia in a human subject, said method comprising:

analyzing nucleic acid of chromosome 9q of said subject for polymorphisms linked to torsion dystonia wherein said polymorphisms are selected from the group consisting of the GSN polymorphism, the D9S10 polymorphism, and polymorphisms which lie between polymorphisms GSN and D9S10; and correlating the presence of said polymorphisms with the presence of said haplotype such that said haplotype is detected.

2. The method of claim 1 wherein said haplotype is 4A12.

3. The method of claim 1, wherein at least one of said polymorphisms is associated with a (GT)n repeat region.

4. A method for determining the propensity of an individual to develop torsion dystonia, said method comprising;:

analyzing nucleic acid of chromosome 9q of said individual to determine the haplotype of said individual wherein said nucleic acid is the GSN or D9S 10 polymorphism or lies between polymorphisms GSN and D9S10, and comparing the haplotype of said individual with a haplotype which is predictive for torsion dystonia, wherein when said haplotypes are the same, the individual has a propensity for developing torsion dystonia.

5. The method of claim 4, wherein said haplotype is 4A12.

6. The method of claim 1, wherein said nucleic acid is DNA.

7. The method of claim 1, wherein said nucleic acid is RNA.

8. The method of claim 6, wherein at least one of said polymorphisms is a restriction fragment length polymorphism (RFLP).

9. The method of claim 8, wherein said analyzing is carried out by the method comprising:

(a) digesting DNA from said subject with a restriction endonuclease enzyme;

(b) electrophoretically separating fragments obtained from said digestion;

(c) detecting said RFLP with a hybridization probe which hybridizes to and identifies said RFLP, thereby generating a restriction pattern; and (d) correlating the presence or absence of said RFLP in said digest with the respective presence or absence of a gene linked with torsion dystonia.

10. The method of claim 9, wherein said probe is detectably labeled.

11. The method of claim 9, wherein at least two different digestions with two different restriction endonuclease enzymes are carried out.

12. The method of claim 9, wherein said restriction pattern for said subject is compared with tile corresponding restriction pattern for family members showing segregation between torsion dystonia and said RFLP.

13. The method of claim 12, wherein said restriction pattern for said subject is compared to a restriction pattern for a parent of said subject which is unaffected by torsion dystonia, a parent of said subject which is affected by torsion dystonia, and a sibling of said subject which is affected by torsion dystonia.

14. The method of claim 9 wherein said probe is radiolabeled M1D.

15. The method of claim 1, wherein said analyzing is carried out by the method comprising:

(a) amplifying nucleic acid from chromosome 9q of said subject;

(b) sequencing said amplified nucleic acid; and (c) correlating the presence or absence of a gene linked with torsion dystonia with the sequence of the amplified nucleic acid.

16. The method of claim 15, wherein said nucleic acid is DNA.

17. The method of claim 16, wherein said DNA is amplified by polymerase chain reaction.

18. The method of claim 15, wherein said nucleic acid is RNA.

19. The method of claim 18, wherein said RNA is amplified with QB-replicase.

20. A method for determining the probability of a human subject developing torsion dystonia, said method comprising:

(a) analyzing nucleic acid of chromosome 9q of family members of said subject to locate polymorphic markers to determine genetic coupling between said markers and the dystonia locus wherein said nucleic acid comprises the GSN or D9S10 polymorphism or lies between the GSN and D9S 10 polymorphisms;

(b) performing linkage analysis for said polymorphic markers to determine genetic coupling between said markers and the torsion dystonia locus;

(c) analyzing nucleic acid of chromosome 9q of said subject to determine the presence or absence of said markers; and (d) determining the probability of said human subject developing torsion dystonia, wherein said probability is measured by the presence or absence of said markers.

21. The method of claim 20, wherein said nucleic acid is DNA or RNA.

22. The method of claim 20, wherein said linkage analysis is performed by the Lod score method.

23. The method of claim 9, wherein more, than one probe is utilized to detect RFLP's.

* * * * *